US009040496B2

(12) United States Patent
Judge et al.

(10) Patent No.: US 9,040,496 B2
(45) Date of Patent: May 26, 2015

(54) REDUCTION OF ALMS1 GENE EXPRESSION OR INHIBITION OF ALTRÖM PROTEIN TO INDUCE CARDIOMYOCYTE PROLIFERATION

(71) Applicant: THE JOHNS HOPKINS UNIVERSITY, Baltimore, MD (US)

(72) Inventors: Daniel Philip Judge, Baltimore, MD (US); Peter Andersen, Baltimore, MD (US); Lincoln Takura Shenje, Portland, OR (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/089,833

(22) Filed: Nov. 26, 2013

(65) Prior Publication Data

US 2014/0179763 A1 Jun. 26, 2014

Related U.S. Application Data

(60) Provisional application No. 61/730,312, filed on Nov. 27, 2012.

(51) Int. Cl.
*A61K 48/00* (2006.01)
*C07H 21/02* (2006.01)
*C07H 21/04* (2006.01)
*C12N 15/11* (2006.01)
*C12N 15/113* (2010.01)

(52) U.S. Cl.
CPC .......... *C12N 15/1136* (2013.01); *C12N 15/113* (2013.01); *C12N 2310/14* (2013.01)

(58) Field of Classification Search
USPC .......................................................... 514/44
See application file for complete search history.

(56) References Cited

U.S. PATENT DOCUMENTS

2005/0214757 A1* 9/2005 Wilson et al. ..................... 435/6

OTHER PUBLICATIONS

Shenje et al. (Nature Communications, 2014 vol. 5:3416).*
Hammond et al. (Nature Review. Genetics. 2001 vol. 2:110-119).*
Collin, G., et al., "Mutations in ALMS1 cause obesity, type 2 diabetes and neurosensory degeneration in Alstrom syndrome", Nat Genet 31, 74-8 (2002).
Marshall, J., et al., "Marshall, J.D. et al. Spectrum of ALMS1 variants and evaluation of genotype-phenotype correlations in Alstrom syndrome", Hum Mutat 28, 1114-23 (2007).
Girard, D., et al., "Alstrom syndrome: insights into the pathogenesis of metabolic disorders", Nat Rev Endocrinol 7, 77-88 (2011).
Marshall, J., et al., "Alstrom syndrome: genetics and clinical overview" Curr Genomics 12, 225-35 (2011).
Bond, J., et al., "The importance of seeking ALMS1 mutations in infants with dilated cardiomyopathy", J Med Genet 42, 10 (2005).
Collin, G., et al., "Alms1-disrupted mice recapitulate human Alstrom syndrome" Hum Mol Genet 14, 2323-33 (2005).
Knorz, V., et al., "Centriolar association of ALMS1 and likely centrosomal functions of the ALMS motif-containing proteins C10or190 and KIAA1731", Mol Biol Cell 21, 3617-29 (2010).

(Continued)

*Primary Examiner* — Terra Cotta Gibbs
(74) *Attorney, Agent, or Firm* — Johns Hopkins Technology Transfer

(57) ABSTRACT

The present invention relates to the field of cardiology. More specifically, the present invention provides methods and compositions for inducing proliferation of cardiomyocytes. In a specific embodiment, a method for inducing proliferation of cardiomyocytes comprises the step of administering an effective amount of an ALMS1 inhibitor.

6 Claims, 12 Drawing Sheets

(56) References Cited

OTHER PUBLICATIONS

Collin, G., et al., "The Alström Syndrome Protein, ALMS1, Interacts with α-Actinin and Components of the Endosome Recycling Pathway", PLoS One 7, e37925 (2012).

Jagger, D., et al., "Alstrom Syndrome protein ALMS1 localizes to basal bodies of cochlear hair cells and regulates cilium-dependent planar cell polarity", Hum Mol Genet 20, 466-81 (2011).

Jatti, K., et al., "Coronary artery disease in Alstrom syndrome", Eur J Hum Genet. Jan. 2012; 20(1): 117-118.

Loudon, M., et al., "Cardiac magnetic resonance imaging in Alstrom syndrome", Orphanet J Rare Dis., Jun. 10, 2009: 4:14.

Davis, E., et al., "Cell polarization defects in early heart development", Circ Res. Jul. 20, 2007; 101(2):122-124.

* cited by examiner

REDUCTION OF ALMS1 GENE EXPRESSION OR INHIBITION OF ALTRÖM PROTEIN TO INDUCE CARDIOMYOCYTE PROLIFERATION

CROSS-REFERENCE TO RELATED APPLICATIONS

This application claims the benefit of U.S. Provisional Application No. 61/730,312, filed Nov. 27, 2012; which is incorporated herein by reference in its entirety.

FIELD OF THE INVENTION

The present invention relates to the field of cardiology. More specifically, the present invention provides methods and compositions for inducing proliferation of cardiomyocytes.

This application contains a sequence listing. It has been submitted electronically via EFS-Web as an ASCII text file entitled "P1178-03$_{13}$ ST25.txt." The sequence listing is 902 bytes in size, and was created on Feb. 27, 2014. It is hereby incorporated by reference in its entirety.

BACKGROUND OF THE INVENTION

Mammalian cardiac development requires continuous proliferation of cardiomyocytes throughout gestation (1, 2). During the perinatal period, cardiomyocyte proliferation rapidly declines, and the majority of cardiomyocytes undergo cell cycle arrest with terminal differentiation (3, 4). Postnatal arrest of the cardiomyocyte cell cycle is a key event for maturation of the mammalian heart, but this process is poorly understood (3).

Mitogenic cardiomyopathy is a very rare form of pediatric cardiomyopathy characterized by persistent markers of mitotic activity at high levels in cardiomyocytes (5). Among five previously reported infants with this condition, there were two pairs of siblings, one of whom had parental consanguinity supporting a recessive genetic disorder. Recently, persistent postnatal cardiomyocyte division was demonstrated in mice lacking the transcription factor Meis (16). However, no naturally inherited conditions associated with delayed postnatal cardiomyocyte cell cycle arrest have previously been characterized in humans. Recognition and characterization of such a disorder has the potential to identify important regulators of the transition of cardiomyocytes from active proliferation to terminal differentiation.

In this study, we identify ALMS1 mutations in 2 siblings and 4 previously reported infants with mitogenic cardiomyopathy. We show that knockdown of murine Alms1 increases cell cycle progression in cultured neonatal murine cardiomyocytes. Likewise, Alms1 knockdown increases the number of induced cardiomyocytes in cultured cells. At postnatal day 15 (1 week beyond the normal murine window of postnatal cardiomyocyte cell cycle arrest), ALMS1-deficient mice show persistent cardiomyocyte proliferation, indicating that ALMS1-deficient cardiomyocytes may have an impaired terminal differentiation of cardiomyocytes.

SUMMARY OF THE INVENTION

The present invention is based, at least in part, on the discovery that suppression of ALMS1 activity induces proliferation of cardiomyocytes. Most cells in the human body are replaced by cell division, but heart cells (cardiomyocytes) are one exception, with very little division or proliferation after birth. The process that leads to loss of cell division postnatally in human heart cells was previously not known. As described herein, the present inventors identified 2 infant siblings with perinatal cardiomyopathy and ongoing proliferation of heart cells at 3 and 5 months after birth (8-fold higher than an age-matched control), and concomitant ALMS1 mutations. The ALMS1 gene was suppressed in cultured mouse cardiomyocytes by siRNA, and a 2.5-fold increase in the number of dividing cardiomyocytes was identified, as well as a 39% increase in cardiomyocytes in phases G2 or M of the cell cycle. Suppression of this gene caused a 10% increase in the number of cardiomyocytes. Mice with targeted mutation in the ALMS1 gene were analyzed, and a 1.8-fold increase in the number of dividing heart cells was identified.

Accordingly, a method to cause heart cells to divide and proliferate after birth is provided herein. Methods that may be used to suppress expression of ALMS1 include siRNA (small interfering ribonucleic acids), antisense oligonucleotides, micro RNA, short hairpin RNA (shRNA), or targeted ALMS1 gene methylation. Methods that may be used to block Alström protein include targeted neutralizing antibodies and small molecules or drugs. Applications of these technologies may be useful to repair heart size or function, to help hearts respond better to injury such as myocardial infarction, to help repair congenital heart defects such as hypoplastic left heart syndrome or septal defects (holes in the heart). Methods to decrease expression of ALMS1 or to interfere with the function of Alström protein could be used to treat heart failure, cardiomyopathy, congenital heart disease, or cardiac injury. In each case, proliferation of cardiomyocytes would lead to more normal heart cells, compensating for the dysfunction in the heart or to abnormal cardiac development.

Thus, in one aspect, the present invention provides compositions and methods for inducing proliferation of cardiomyocytes. In a specific embodiment, a method for inducing proliferation of cardiomyocytes comprises the step of administering an effective amount of an ALMS1 inhibitor. In a more specific embodiment, the ALMS1 inhibitor inhibits ALMS1 expression. In another specific embodiment, the ALMS1 inhibitor inhibits ALMS biological activity.

In another embodiment, a method for treating heart failure, cardiomyopathy, congenital heart disease or cardiac injury in a patient comprises the step of administering to the patient a therapeutically effective amount of an ALMS1 inhibitor, wherein the ALMS1 inhibitor inhibits ALMS1 expression and/or activity and induces proliferation of cardiomyocytes. In yet another embodiment, a method for inducing proliferation of cardiomyocytes in a patient suffering from heart failure, cardiomyopathy, congenital heart disease or cardiac injury comprises the step of administering to the patient a therapeutically effective amount of an ALMS1 inhibitor.

In particular embodiments, the ALMS1 inhibitor is a small molecule, an antibody, a protein, a peptide, or a nucleic acid. In a specific embodiment, the nucleic acid is an siRNA.

DETAILED DESCRIPTION OF THE INVENTION

Figure 1:
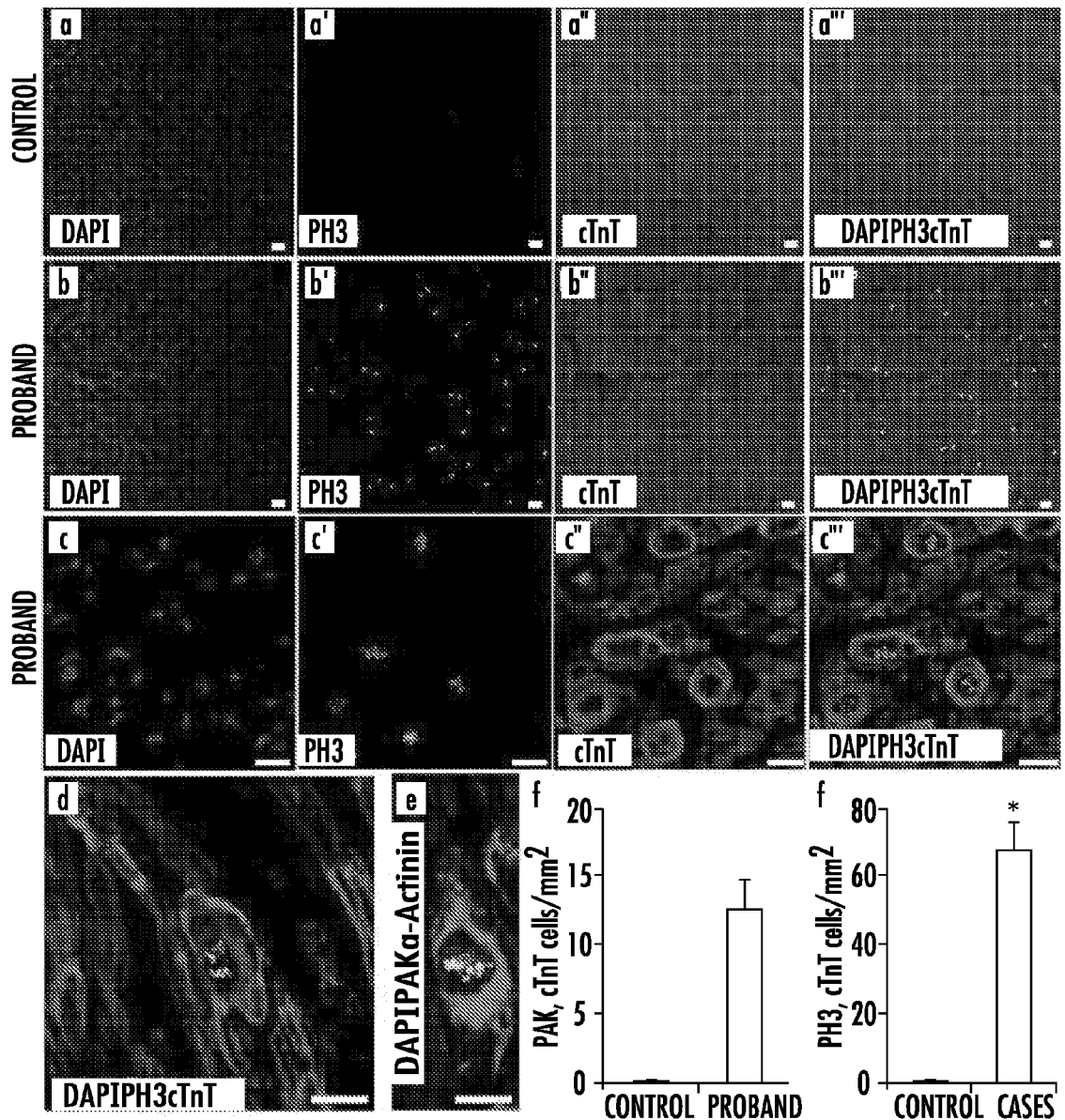
FIG. 1. Increased cardiomyocyte proliferation in people with ALMS1 mutations. (A, B). Representative confocal images of the proband heart vs. age-matched control. (C) Higher magnification confocal images of PH3-positive cardiomyocytes in the proband (D) Additional high-magnification confocal image of a PH3-positive cardiomyocyte in the proband. (E) Phospho-aurora kinase (PAK) staining is present in a dividing cardiomyocyte nucleus in the proband (F) The number of PAK-positive cardiomyocytes in the heart of the proband was compared to three age-matched controls with failing ventricles. (G) The number of PH3-positive cardiomyocytes in affected individuals was compared to three age-matched controls with failing ventricles. Error bars represent standard error of mean (SEM). All scale bars represent 10 µm.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Cardiomyocyte cell division and replication in mammals proceed normally through embryonic development and abruptly decline soon after birth. The process governing this terminal differentiation of cardiomyocytes is incompletely understood. In an infant with evidence of persistent postnatal cardiomyocyte replication, we applied whole exome sequencing to determine the cause. We identified compound heterozygous ALMS1 mutations in the proband, and confirmed their presence in her affected sibling, one copy inherited from each heterozygous parent. Next, we recognized homozygous or compound heterozygous truncating mutations in ALMS1 in four other children with high levels of postnatal cardiomyocyte proliferation. Knockdown of Alms1 was sufficient for extension of cardiomyocyte proliferation in vitro. Homozygous Alms1-mutant mice have impaired neonatal cardiomyocyte cell cycle arrest. ALMS1 encodes Alström protein, a component of the non-motile primary cilium. We conclude that deficiency of Alström protein impairs postnatal cardiomyocyte cell cycle arrest.

I. Definitions

The following definitions are used throughout this specification. Other definitions are embedded within the specification for ease of reference.

The term "ALMS1 inhibitor" refers to an agent that inhibits the synthesis or biological activity of Alström syndrome 1 (Alström) protein. The term includes compounds that have activity in addition to ALMS1 inhibitory activity. The term is used interchangeably with "Alström protein inhibitor," and the like.

As used herein, the term "effective," means adequate to accomplish a desired, expected, or intended result. More particularly, a "therapeutically effective amount" as provided herein refers to an amount of an ALMS1 inhibitor of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a ALMS1 inhibitor, necessary to provide the desired therapeutic effect, e.g., an amount that is effective to prevent, alleviate, or ameliorate symptoms of disease or prolong the survival of the subject being treated. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against ALMS1 and used as ALMS1 inhibitors. In other embodiments, antibodies may be raised against ALMS1 protein/peptides that have undergone post-translational modification(s).

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Optional" or "optionally" means that the subsequently described event or circumstance can or cannot occur, and that the description includes instances where the event or circumstance occurs and instances where it does not.

As used herein, a "subject" or "patient" means an individual and can include domesticated animals, (e.g., cats, dogs, etc.); livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. In particular, the term also includes mammals diagnosed with cardiac hypertrophy.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

II. ALMS1 Inhibitors

A. RNA Interference Compositions for Targeting ALMS1 mRNAs

In one aspect of the present invention, the expression of ALMS1 may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al., 10 MOL. CELL. 549-61 (2002); Elbashir et al., 411 Nature 494-98 (2001)), micro-RNAs (miRNA), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99(9) PROC. NATL. ACAD. SCI. USA, 6047-52 (2002); McManus et al., 8 RNA 842-50 (2002); Sui et al., 99(6) PROC. NATL. ACAD. SCI. USA 5515-20 (2002). The nucleic acid and amino acid sequence of ALMS1 is known in the art and readily available. See Entrez, Gene ID: 7840, updated on 3 Nov. 2013; and UniProt, Q8TCU4 (ALMS1_HUMAN), both of which sequences are incorporated herein by reference.

1. Small Interfering RNA

In particular embodiments, the present invention features "small interfering RNA molecules" ("siRNA molecules" or "siRNA"), methods of making siRNA molecules and methods for using siRNA molecules (e.g., research and/or therapeutic methods). The siRNAs of this invention encompass any siRNAs that can modulate the selective degradation of ALMS1 mRNA.

In a specific embodiment, the siRNA of the present invention may comprise double-stranded small interfering RNA molecules (ds-siRNA). A ds-siRNA molecule of the present invention may be a duplex made up of a sense strand and a complementary antisense strand, the antisense strand being sufficiently complementary to a target ALMS1 mRNA to mediate RNAi. The siRNA molecule may comprise about 10 to about 50 or more nucleotides. More specifically, the siRNA molecule may comprise about 16 to about 30, e.g., 16, 17, 18, 19, 20, 21, 22, 23, 24, 25, 26, 27, 28, 29, or 30 nucleotides in each strand. The strands may be aligned such that there are at least 1, 2, or 3 bases at the end of the strands which do not align (e.g., for which no complementary bases occur in the opposing strand) such that an overhang of 1, 2 or 3 residues occurs at one or both ends of the duplex when strands are annealed.

In an alternative embodiment, the siRNA of the present invention may comprise single-stranded small interfering RNA molecules (ss-siRNA). Similar to the ds-siRNA molecules, the ss-siRNA molecule may comprise about 10 to about 50 or more nucleotides. More specifically, the ss-siRNA molecule may comprise about 15 to about 45 or more nucleotides. Alternatively, the ss-siRNA molecule may comprise about 19 to about 40 nucleotides. The ss-siRNA molecules of the present invention comprise a sequence that is "sufficiently complementary" to a target mRNA sequence to direct target-specific RNA interference (RNAi), as defined herein, e.g., the ss-siRNA has a sequence sufficient to trigger the destruction of the target mRNA by the RNAi machinery or process. In one embodiment, the ss-siRNA molecule can be designed such that every residue is complementary to a residue in the target molecule. Alternatively, substitutions can be made within the molecule to increase stability and/or enhance processing activity of the molecule. Substitutions can be made within the strand or can be made to residues at the ends of the strand. In a specific embodiment, the 5'-terminus may be phosphorylated (e.g., comprises a phosphate, diphosphate, or triphosphate group). In another embodiment, the 3' end of an siRNA may be a hydroxyl group in order to facilitate RNAi, as there is no requirement for a 3' hydroxyl group when the active agent is a ss-siRNA molecule. In other instances, the 3' end (e.g., C3 of the 3' sugar) of ss-siRNA molecule may lack a hydroxyl group (e.g., ss-siRNA molecules lacking a 3' hydroxyl or C3 hydroxyl on the 3' sugar (e.g., ribose or deoxyribose).

In another aspect, the siRNA molecules of the present invention may be modified to improve stability under in vitro and/or in vivo conditions, including, for example, in serum and in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

Furthermore, the siRNAs of the present invention may include modifications to the sugar-phosphate backbone or nucleosides. These modifications can be tailored to promote selective genetic inhibition, while avoiding a general panic response reported to be generated by siRNA in some cells. In addition, modifications can be introduced in the bases to protect siRNAs from the action of one or more endogenous enzymes.

In an embodiment of the present invention, the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues. Examples of nucleotide analogues include sugar- and/or backbone-modified ribonucleotides (e.g., include modifications to the phosphate-sugar backbone). For example, the phosphodiester linkages of natural RNA may be modified to include at least one of a nitrogen or sulfur heteroatom. In backbone-modified ribonucleotides, the phosphoester group connecting to adjacent ribonucleotides may be replaced by a modified group, e.g., a phosphothioate group. In sugar-modified ribonucleotides, the 2' OH-group may be replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Nucleobase-modified ribonucleotides may also be utilized, e.g., ribonucleotides containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. It should be noted that the above modifications may be combined.

Derivatives of siRNAs may also be utilized herein. For example, cross-linking can be employed to alter the pharmacokinetics of the composition, e.g., to increase half-life in the body. Thus, the present invention includes siRNA derivatives that include siRNA having two complementary strands of nucleic acid, such that the two strands are crosslinked. The present invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The siRNAs of the present invention can be enzymatically produced or totally or partially synthesized. Moreover, the siRNAs can be synthesized in vivo or in vitro. For siRNAs that are biologically synthesized, an endogenous or a cloned exogenous RNA polymerase may be used for transcription in vivo, and a cloned RNA polymerase can be used in vitro. siRNAs that are chemically or enzymatically synthesized are preferably purified prior to the introduction into the cell.

Although one hundred percent (100%) sequence identity between the siRNA and the target region is preferred in particular embodiments, it is not required to practice the invention. siRNA molecules that contain some degree of modification in the sequence can also be adequately used for the purpose of this invention. Such modifications may include, but are not limited to, mutations, deletions or insertions, whether spontaneously occurring or intentionally introduced.

Moreover, not all positions of a siRNA contribute equally to target recognition. In certain embodiments, for example, mismatches in the center of the siRNA may be critical and could essentially abolish target RNA cleavage. In other embodiments, the 3' nucleotides of the siRNA do not contribute significantly to specificity of the target recognition. In particular, residues 3' of the siRNA sequence which is complementary to the target RNA (e.g., the guide sequence) may not critical for target RNA cleavage.

Sequence identity may be determined by sequence comparison and alignment algorithms known to those of ordinary skill in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (e.g., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (e.g., a local alignment). A non-limiting example of a local alignment algorithm utilized for the comparison of sequences is the algorithm of Karlin and Altschul, 87 Proc. Natl. Acad. Sci. USA 2264-68 (1990), and as modified as in Karlin and Altschul 90 Proc. Natl. Acad. Sci. USA 5873-77 (1993). Such an algorithm is incorporated into the BLAST programs (version 2.0) of Altschul, et al., 215 J. Mol. Biol. 403-10 (1990).

In another embodiment, the alignment may optimized by introducing appropriate gaps and determining percent identity over the length of the aligned sequences (e.g., a gapped alignment). To obtain gapped alignments for comparison purposes, Gapped BLAST can be utilized as described in Altschul et al., 25(17) Nucleic Acids Res. 3389-3402 (1997). In another embodiment, the alignment may be optimized by introducing appropriate gaps and determining percent identity over the entire length of the sequences aligned (e.g., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In particular embodiments, greater than 90% sequence identity, e.g., 91%, 92%, 93%, 94%, 95%, 96%, 97%, 98%, 99% or even 100% sequence identity, between the siRNA and the portion of the target gene may be used. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional hybridization conditions include, but are not limited to, hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length can be about 5-10° C. less than the melting temperature (Tm) of the hybrid, where Tm is determined according to the following equations. For hybrids less than 18 base pairs in length, $Tm(°C.)=2(\# \text{ of } A+T \text{ bases})+4(\# \text{ of } G+C \text{ bases})$. For hybrids between 18 and 49 base pairs in length, $Tm(°C.)=81.5+16.6(\log 10[Na^+])+0.41(\% G+C)-(600/N)$, where N is the number of bases in the hybrid, and $[Na^+]$ is the concentration of sodium ions in the hybridization buffer ($[Na^+]$ for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 50 or more bases.

2. Other Compositions for Targeting ALMS1 DNA or mRNA

Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site, impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins. An example of an antisense oligonucleotide of the present invention is a cDNA that, when introduced into a cell, transcribes into an RNA molecule having a sequence complementary to at least part of the ALMS1 mRNA.

Furthermore, antisense oligonucleotides of the present invention include oligonucleotides having modified sugar-phosphodiester backbones or other sugar linkages, which can provide stability against endonuclease attacks. The present invention also encompasses antisense oligonucleotides that are covalently attached to an organic or other moiety that increase their affinity for a target nucleic acid sequence. For example, intercalating agents, alkylating agents, and metal complexes can be also attached to the antisense oligonucleotides of the present invention to modify their binding specificities.

The present invention also provides ribozymes as a tool to inhibit ALMS1 expression. Ribozymes are enzymatic RNA molecules capable of catalyzing the specific cleavage of RNA. The characteristics of ribozymes are well-known in the art. See, e.g., Rossi, 4 CURRENT BIOLOGY 469-71 (1994). Without being limited by theory, the mechanism of ribozyme action involves sequence specific hybridization of the ribozyme molecule to complementary target RNA, followed by an endonucleolytic cleavage. In particular embodiments, the ribozyme molecules include one or more sequences complementary to the target gene mRNA, and include the well-known catalytic sequence responsible for mRNA cleavage. See U.S. Pat. No. 5,093,246. Using the known sequence of the target ALMS1 mRNA, a restriction enzyme-like ribozyme can be prepared using standard techniques.

The expression of the ALMS1 gene can also be inhibited by using triple helix formation. Nucleic acid molecules to be used in triple helix formation for the inhibition of transcription can be single stranded and composed of deoxynucleotides. The base composition of these oligonucleotides must be designed to promote triple helix formation via Hoogsteen base paring rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3',3'-5' manner, such that they base pair first with one strand of a duplex and then the other, eliminating the necessity for a sizeable stretch of either purines or pyrimidines to be present on one strand of a duplex.

The expression of ALMS1 may be also inhibited by what is referred to as "co-repression." Co-repression refers to the phenomenon in which, when a gene having an identical or similar to the target sequence is introduced to a cell, expression of both introduced and endogenous genes becomes repressed. This phenomenon, although first observed in plant system, has been observed in certain animal systems as well. The sequence of the gene to be introduced does not have to be identical to the target sequence, but sufficient homology allows the co-repression to occur. The determination of the extent of homology depends on individual cases, and is within the ordinary skill in the art.

It would be readily apparent to one of ordinary skill in the art that other methods of gene expression inhibition that selectively target ALMS1 DNA or mRNA can also be used in connection with this invention without departing from the spirit of the invention. In a specific embodiment, using techniques known to those of ordinary skill in the art, the present invention contemplates affecting the promoter region of ALMS1 to effectively switch off transcription.

3. Design and Production of the RNAi Compositions

One or more of the following guidelines may be used in designing the sequence of siRNA and other nucleic acids designed to bind to a target mRNA, e.g., shRNA, stRNA, microRNA, antisense oligonucleotides, ribozymes, and the like, that are advantageously used in accordance with the present invention.

Beginning with the AUG start codon of the ALMS1 gene, each AA dinucleotide sequence and the 3' adjacent 16 or more nucleotides are potential siRNA targets. In a specific embodiment, the siRNA is specific for a target region that differs by at least one base pair between the wild type and mutant allele or between splice variants. In dsRNAi, the first strand is complementary to this sequence, and the other strand identical or substantially identical to the first strand. siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules may have a 3' overhang of 2 nucleotides, such as TT. The overhanging nucleotides may be either RNA or DNA. In one embodiment, it may be desirable to choose a target region wherein the mismatch is a purine:purine mismatch.

Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website (http://www.ncbi.nih.gov). Select one or more sequences that meet the criteria for evaluation.

Another method includes selecting in the sequence of the target mRNA, a region located from about 50 to about 100 nt 3' from the start codon. In this region, search for the following sequences: AA(N19)TT(SEQ ID NO:1) or AA(N21) (SEQ ID NO:2), where N=any nucleotide. The GC content of the selected sequence should be from about 30% to about 70%, preferably about 50%. To maximize the specificity of the RNAi, it may be desirable to use the selected sequence in a search for related sequences in the genome of interest; sequences absent from other genes are preferred. The secondary structure of the target mRNA may be determined or predicted, and it may be preferable to select a region of the mRNA that has little or no secondary structure, but it should be noted that secondary structure seems to have little impact on RNAi. When possible, sequences that bind transcription and/or translation factors should be avoided, as they might competitively inhibit the binding of a siRNA, sbRNA or stRNA (as well as other antisense oligonucleotides) to the mRNA. Further general information about the design and use of siRNA may be found in "The siRNA User Guide," available at The Max-Planck-Institut fur Biophysikalishe Chemie website (http://www.mpibpc.mpg.de).

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome.

4. Delivery of ALMS1 RNA Targeting Compositions

Delivery of the compositions of the present invention (e.g., siRNAs, antisense oligonucleotides, or other compositions described herein) into a patient can either be direct, e.g., the patient is directly exposed to the compositions of the present invention or compound-carrying vector, or indirect, e.g., cells are first transformed with the compositions of this invention in vitro, then transplanted into the patient for cell replacement therapy. These two approaches are known as in vivo and ex vivo therapy, respectively.

In the case of in vivo therapy, the compositions of the present invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector, by direct injection of naked DNA, by coating with lipids or cell-surface receptors or transfecting agents, encapsulation in liposomes, nanoparticles, microparticles, or microcapsules, by administering them in linkage to a peptide which is known to enter the cell or nucleus, or by administering them in linkage to a ligand subject to receptor-mediated endocytosis which can be used to target cell types specifically expressing the receptors. Further, the compositions of the present invention can be targeted in vivo for cell specific uptake and expression, by targeting a specific receptor. See, e.g., WO93/14188, WO 93/20221, WO 92/22635, WO92/20316, and WO 92/06180.

Ex vivo therapy involves transferring the compositions of the present invention to cells in tissue culture by methods well-known in the art such as electroporation, transfection, lipofection, microinjection, calcium phosphate mediated transfection, cell fusion, chromosome-mediated gene transfer, microcell-mediated gene transfer, spheroplast fusion, and infection with a viral vector containing the nucleic acid sequences. These techniques should provide for the stable transfer of the compositions of this invention to the cell, so that they are expressible by the cell and preferably heritable and expressible by its cell progeny. In particular embodiments, the method of transfer includes the transfer of a selectable marker to the cells. The cells are then placed under selection to isolate those cells that have taken up and are expressing the transferred compositions. The resulting recombinant cells can be delivered to a patient by various methods known in the art. Examples of the delivery methods include, but are not limited to, subcutaneous injection, skin graft, and intravenous injection.

B. Antibodies to ALMS1

The present invention contemplates the use of antibodies specific for ALMS1, for example, to repair heart size or function, to help hearts respond better to injury such as myocardial infarction, to help repair congenital heart defects such as hypoplastic left heart syndrome or septal defects (holes in the heart). The phrases "binding specificity," "binding specifically to," "specific binding" or otherwise any reference to an antibody to ALMS1, refers to a binding reaction that is determinative of the presence of the corresponding ALMS1 antigen to the antibody in a heterogeneous population of antigens and other biologics. The parameters required to achieve such specificity can be determined routinely, using conventional methods in the art including, but not limited to, competitive binding studies. The binding affinity of an antibody can also be readily determined, for example, by Scatchard analysis (Scatchard, Ann. NY Acad. Sci. 51: 660-672, 1949). In some embodiments, the immunoglobulins of the present invention bind to ALMS1 at least about 5, at least about 10, at least about 100, at least about $10^3$, at least about $10^4$, at least $10^5$, and at least $10^6$ fold higher than to other proteins.

Various procedures known in the art may be used for the production of antibodies to ALMS1 or a fragment, derivative, homolog or analog of the protein. Antibodies of the present invention include, but are not limited to, synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

In some embodiments, an antibody specifically binds an epitope of the ALMS1 protein. It is to be understood that the peptide regions may not necessarily precisely map one epitope, but may also contain an ALMS1 sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., 157 J. MOL. BIOL. 105-32 (1982)); Hopp and Woods Analysis (Hopp, T. P. and Woods, K. R., 78 PROC. NATL. ACAD. SCI. USA 3824-28 (1981); Hopp, T. J. and Woods, K. R., 20 MOL. IMMUNOL. 483-89 (1983); Hopp, T. J., 88 J. IMMUNOL. METHODS 1-18 (1986)); Jameson-Wolf Analysis (Jameson, B. A. and Wolf, H., 4 COMPUT. APPL. BIOSCI. 181-86 (1988)); and Emini Analysis (Emini et al., 140 VIROLOGY 13-20 (1985)).

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the ALMS1 antibodies that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identify contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half-life of an antibody, one may incorporate a salvage receptor binding epitope into the antibody (especially an immunoglobulin fragment) as described in, for example, U.S. Pat. No. 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-ALMS1 antibodies of the present invention.

C. Small Molecule Inhibitors of ALMS1 & Compound Libraries

In other embodiments, the ALMS1 inhibitor is a small molecule. The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Compound libraries may be screened for ALMS1 inhibitors. A compound library is a mixture or collection of one or more putative inhibitors generated or obtained in any manner. Any type of molecule that is capable of interacting, binding or has affinity for ALMS1 may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as small molecule organic compounds generated, for example, using combinatorial chemistry techniques; and mixtures thereof.

A library typically contains more than one putative inhibitor or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to about 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation, A-Syntese-Biotech ApS, Akos-SC, G & J Research Chemicals Ltd., Life Chemicals, Interchim S.A., and Spectrum Info. Ltd.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

DNA Extraction, Library Preparation and Whole Exome Enrichment. Genomic DNA was obtained from the proband's dermal fibroblasts and from blood from each of the parents by the Gentra Puregene Tissue/Blood Kit (Qiagen). Three μg of genomic DNA was sheared using the Covaris S-2 instrument (Covaris) using the recommended settings according to the Agilent protocol (SureSelectXT Target enrichment System for Illumina Paired End and Multiplexed Sequencing Library v1.0) for a 150-200 bp fragment size. Libraries were prepared for targeted enrichment using the SPRIworks Fragment Library System I (200-400 bp size selection) according to Beckman-Coulter's protocol (version 2.0). Adapter ligated fragments were amplified according to the Agilent protocol for 6 cycles; 500 ng of amplified library was used in a whole exome enrichment reaction with the SureSelect Human All Exon, 50 Mb product (Agilent WE). Samples were clustered one per flow cell lane using the Illumina cBot Paired End Cluster Generation Kit with v1 HiSeq flow cell (Illumina) Seventy-six by paired-end sequencing was performed on the HiSeq2000 with TruSeq SBS v1 chemistry (Illumina).

Primary Analysis. Intensity analysis and base calling were performed through the Illumina Real Time Analysis (RTA) software (version 1.7.48.0). Average sequence yield for the samples was 9.2 Gb having a quality value of Q30 or greater. Basecall files were converted from a binary format (BCL) to flat file format (qseq.txt) using the Illumina BCL Converter software (version 1.7.1).

Secondary Analysis:

DNA Sequence Alignment and Variant Calling: Basecall files were converted to fastq format, aligned with BWA39 version 0.5.7 to the GRCh37 human genome reference. Duplicate molecules were flagged with Picard version 1.26.

SNVs and indels were called using SAMtools40 version 0.1.7. Only variant calls from the reference genome having a minimum depth of 10× were considered for downstream analysis. In addition, for SNVs, only those calls where the root mean square of their read mapping qualities (RMS) was greater than 20 were considered while for indels only those with an RMS greater than 15 were considered.

Sample QC: Samples were processed on the Illumina Infinium HumanOmniExpress beadchip (OE) to confirm family and gender relationships and provide sample identity confirmation against the sequencing data. The mean on bait coverage (regions covered by probes in the Agilent WE) was greater than 77× for each sequencing experiment and greater than 92% of on bait bases had a depth greater than 10×. Overall concordance to genotypes for each sample was greater than 99.5%. Greater than 93% of the OE heterozygote genotypes for each sample within the baited regions were called as variants against reference in the sequencing experiments.

Variant Filtering: All remaining variants were annotated using the SeattleSeq Annotation Server build 6.03 (http://gvs.gs.washington.edu/SeattleSeqAnnotation/). Variants present in dbSNP131 or the 1000 genomes pilot April 2010 dataset were filtered out. Only missense, nonsense or splice site compound heterozygotes present in the offspring where one allele each was inherited from the parents were considered. After this level of filtering, 6 compound missense heterozygotes and 1 compound heterozygote frameshift indel remained.

Cell Culture and Analysis. Mouse neonatal cardiomyocytes were isolated from newborn mouse hearts on PD0.5. Hearts were minced and digested with collagenase type II and pancreatase myocyte digestion buffer. To enrich for cardiomyocytes, dissociated cells were pre-plated by the conventional pre-plating method (20, 41). Enriched cardiomyocytes were cultured in Dulbecco's Modified Eagle Medium (GIBCO) supplemented with 20% horse serum and 2 mM GlutaMAX (Invitrogen) in 5% CO2. Cardiac fibroblasts were identified by their expression of the cardiac fibroblast marker Thy-1 (20, 21). Mouse embryonic stem cells (mESCs) carrying a puromycin resistance cassette driven by the cardiomyocyte-specific sodium-calcium exchanger 1 gene (Ncx1) promoter (42) were maintained and cultured as described 43. For differentiation, ESCs were allowed to form embryoid bodies (EBs) in the IMDM/Ham-F12 (Cellgro) (3:1) supplemented with N2, B27, Penicillin/Streptomycin, 2 mM GlutaMAX, 0.05% BSA, 5 ng/ml L-ascorbic acid (Sigma-Aldrich), α-Monothioglycerol (MTG, Sigma-Aldrich). For mesoderm induction EBs were dissociated and reaggregated in the presence of Activin A, BMP4 and VEGF for 48 hours (44). Cardiomyocytes were selected with Puromycin (2.5 ug/ml) for 48 h as previously described (42), dissociated and counted using an automated cell counter (Scepter 2.0, Millipore).

RNA Suppression and Cell Cycle Analysis. Cardiomyocytes were transfected with Lipofectamine RNAiMAX (Invitrogen). For Alms1 knockdown experiments, Alms1 ON-TARGETplus SMARTpool and Alms1 siRNA (Ambion) or scrambled siRNA oligonucleotides (Dharmacon) and siRNA negative control (Ambion) were used at a final concentration of 100 nM for cell transfection. Forty-eight hours after transfection, cells were fixed and stained for flow cytometry with the following antibodies: anti-Ki67, -phospho-aurora A/B/C kinase, -cardiac troponin T, -Thy1-APC, or -phosphoaurora A/B/C with secondary detection using the appropriate Alexa Fluor-conjugated antibody (Invitrogen). For S-phase analysis, cardiomyocytes were treated with 100 μM EdU for 30 min prior to fixation and stained using Click-iT EdU cell proliferation kit (Invitrogen). For cell cycle analysis, dissociated cardiomyocytes were incubated for 30 mM with 5 μM Vybrant Dye Cycle Ruby Stain (Invitrogen). For EdU analysis, cells were treated with 100 μM EdU for 30 minutes prior to isolation and fixation. EdU incorporation was detected using Click-it EdU Alexa Fluor Imaging Kit (Invitrogen) according to manufacturer's protocol. Cells were analyzed on an Accuri C6 flow cytometer using FlowJo software.

Mice. The Alms1$^{Gt/Gt}$ mice (B6.129P2-Alms1Gt(XH152) Byg/Pjn) used in this study were described previously (24, 45). Mice were fed ad libitum a 4K54 diet (PMI Nutrition International, St. Louis, Mo.) and provided an unlimited access to water in a temperature/humidity controlled setting with a 12 hour light/dark cycle at The Jackson Laboratory Research Animal Facility. All mouse protocols used in this study were approved by the JAX institutional Animal Care and Use Committee. Mouse hearts were extracted from mice euthanized by carbon dioxide asphyxiation and allowed to contract in phosphate buffered saline for 5-10 minutes and immediately placed in 4% paraformaldeyde at 4° C. overnight. Subsequently, tissues were embedded in paraffin, sectioned, and immunostained as previously reported (46). The aMHC promoterdriven EGFP-IRES-puromycin transgenic mice (aMHC-GFP), in which only cardiomyocytes express the green fluorescent protein (GFP) were described previously (Ieda M et al, 2010). Hearts from these mice were dissociated using collagense II/TrypLE. GFP+ cardiomyocytes were isolated by Fluoroscence Activated Cell Sorting (FACS) using a FACS Aria I (BD Biosciences).

Histology and Immunohistochemistry. Paraffin-embedded heart sections were rehydrated, followed by antigen retrieval Immunostaining was performed on cultured cardiomyocytes and mouse cardiac tissue with primary antibodies against Ki67, cardiac troponin T, α-sarcomeric actinin, phosphohistone-H3, phosphoaurora A/B/C, or activated caspase-3 followed by secondary detection with appropriate Alexa Fluor conjugated antibodies. Additional staining was done with wheat germ agglutinin conjugated with Alexa Fluor-647 dye to show cell boundaries. Analyses using confocal microscopy were quantified in a blinded fashion by 2 independent observers. All images were acquired with a Zeiss LSM 510 Meta Confocal system and analyzed with Volocity imaging software. Puromycin selected cardiomyocytes were fixed in 4% formaldehyde. Cardiomyocytes were permabilized with 0.5% saponin/PBS and stained with antibodies against cTnT or isotype control antibodies followed the appropriate Alexa Fluor-conjugated antibody (Invitrogen).

Quantitative qRT-PCR. RNA was extracted with TRIzol (Invitrogen). Reverse transcriptase-quantitative PCR (qPCR) was performed using the Superscript III first-strand synthesis system (Invitrogen) followed by use of TaqMan probes on the ABI 7900HT (Applied Biosystems) according to the manufacturer's protocols. Optimized primers from TaqMan Gene Expression Array were used. Expression levels were normalized to Gapdh expression. All samples were run at least in triplicate. Real-time PCR data were normalized and standardized with SDS2.2 software.

Quantitative Fluorescence. To measure nuclear DNA content, 20 um thick histology sections of the proband's heart were stained with DAPI. Using a Zeiss LSM 510 Meta confocal microscope and Zen software for image acquisition, the nuclear DNA content of cardiac myocytes was assayed by measuring the total fluorescence from each selected nucleus with Volocity™ imaging software. Background fluorescence was excluded prior to image acquisition using Zen software. Nuclei in contact with the edges of the image stack or touching other nuclei were excluded. The total DAPI fluorescence signal associated with diploid status was designated 1 in non-proliferating cells (negative for PH3 staining). The DNA content of proliferating cardiomyocytes (positive for PH3 staining) was compared to non-proliferating cells and displayed as a ratio of the total quantitative fluorescence. A value of 2 would indicate cells that have a full duplication of nuclear DNA prior to karyokinesis.

Statistics. Please see the detailed section on whole exome sequencing and its analysis above. For all other analyses, paired Student's t-tests using 2-sided comparisons were utilized.

Results

Figure 5:
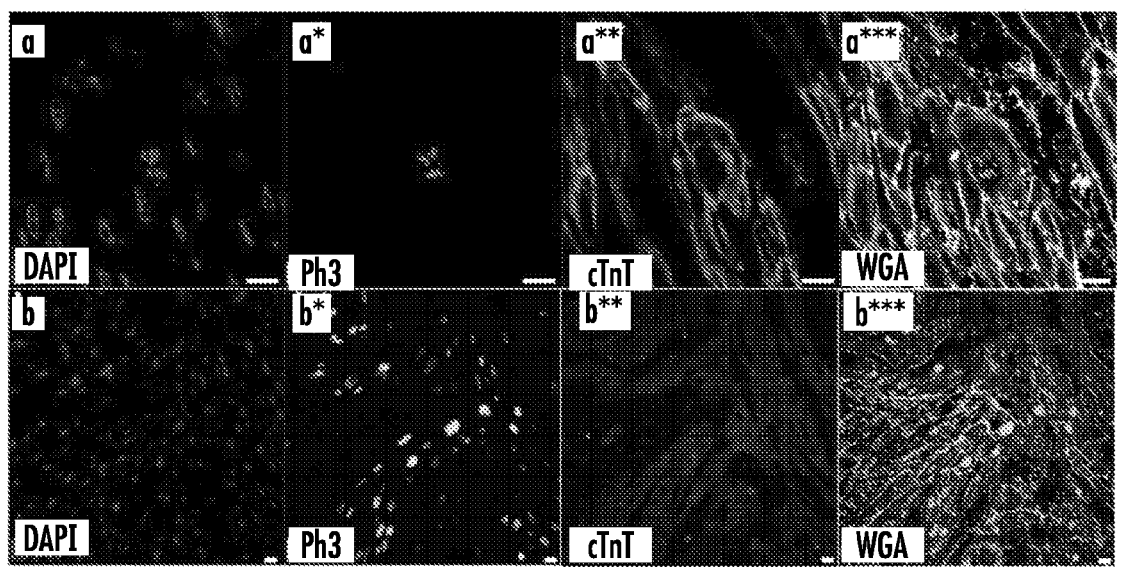
FIG. 5. PH3-positive cardiomyocytes in the proband and another affected individual. Additional representative confocal microscopic images from the heart of the proband (A) and another individual with mitogenic cardiomyopathy (B) have high levels of phosphohistone-H3 (Ph3)-positivity. Images were obtained with confocal microscopy using immunostaining for Ph3, α-sarcomeric actinin or troponin T, wheat germ agglutinin to outline cell boundaries, and DAPI to highlight nuclei.

Mitogenic Cardiomyopathy in the Proband and her Sibling. We identified two infant siblings with neonatal heart failure, both of whom required cardiac transplantation. The proband was normal at birth, and she had no other manifestations of Alström syndrome prior to transplantation, which was performed at three months of age. The proband's only sibling underwent cardiac transplantation at age five months for similar cardiac dysfunction. Intracranial bleeding complicated her post-operative course, and she died one month later. Cardiac evaluations of both parents were normal. We visualized mitotic cardiomyocytes with antibodies against phosphorylated histone H3 (PH3, a marker for M-phase (7)) and cardiac troponin T (cTnT) (FIG. 1a, b, c, and d) and as well as wheat germ agglutinin (WGA) to distinguish cell boundaries (FIG. 5). Using an unbiased double-blinded approach for quantification of proliferating myocytes, we quantified PH3-positive cardiomyocytes in the proband and three age-matched controls with heart failure. The amount of PH3-positive cardiomyocytes was higher in the proband than in the controls (114.3+31.3 per mm$^2$) vs. 0.28+0.07 per mm$^2$, respectively). To validate the high number of proliferating cardiomyocytes in the proband, we stained with antibodies against phospho-aurora kinases (PAK) A, B, and C. PAK A/B/C are important regulators of karyokinesis and cytokinesis, and localization of phospho-aurora kinase B to the cleavage furrow is required for establishing cytokinesis (8). Aurora kinases are essential for formation of the mitotic spindle, separation of centrosomes and assembly of the cleavage furrow during pro-, meta-, ana-, and telophase of mitosis (8-10) Immunostaining for PAK confirmed an increase in the number of positively stained cardiomyocytes in the proband compared to the age-matched controls with heart failure (12.2+2.6 per mm$^2$ vs. <0.02+0.01 per mm$^2$, respectively) (FIG. 1e, f).

The proband underwent clinical genetic testing to determine the cause of her cardiomyopathy with a resequencing array (11). Analysis of MYH7, MYBPC3, TNNT2, TNNI3, TPM1, ACTC, LMNA, SGCD, EMD, DES, LDB3, ACTN2, CSRP3, TCAP, VCL, TAZ, PLN, ABCC9, and CTF1 showed no apparent cause for cardiomyopathy. Next, we performed whole exome sequencing using DNA obtained from the affected proband and both of her parents. With the presumption of a recessive disorder, we focused on missense, nonsense, or splice site variants that were likely to be compound heterozygote mutations in the affected offspring, since the ethnicity of the parents was geographically distant (northern European and Southeast Asian). Variants present in dbSNP131 or the 1000 genomes pilot April 2010 dataset were filtered out. After this level of filtering, six genes with compound missense variants and one gene with compound heterozygote frameshift insertion/deletion remained (Table 1). The 1000 genomes November 2010 data were subsequently available, and three of these genes with previously novel compound heterozygous missense variants were filtered. Sanger sequencing confirmed novel DNA variants in each of the remaining four genes. The absence of one or both variants in the affected sibling led to filtering of two additional genes. FERMT1 had two novel missense alleles (p.Arg98Cys and p.Val519Leu) that were present in each of the affected individuals. These novel variants in FERMT1 were prioritized lower than ALMS1 because Arg98 is not highly conserved (Cys in Danio rerio), and because valine and leucine are both neutral nonpolar amino acids (Grantham score 32); both variants are present at low levels in the NHLBI Exome Variant Server. We identified and confirmed two heterozygous ALMS1 mutations in the proband and her sibling, both of which result in frameshift and premature termination (c.1794_1801 dup8 in exon 8 and c.11116_11134del19 in exon 16). Mutations in ALMS1 are known to cause Alström syndrome, a recessive systemic disorder (12). The c.11116_11134 del19 mutation was previously reported in a patient with Alström syndrome (13). Each parent harbored one of the mutant ALMS1 alleles. Alström syndrome (OMIM #203800) is a recessive ciliopathy caused by ALMS1 mutations and characterized by childhood truncal obesity, insulin-resistant diabetes mellitus, sensorineural hearing loss, retinal degeneration, and systemic fibrosis affecting multiple organs (kidney, liver, lung, and heart) (14, 15). Cardiomyopathy manifests in approximately two-thirds of affected individuals, and it can precede all other manifestations, obscuring the diagnosis of Alström (16, 17). We hypothesized that the mutations in ALMS1 caused the delayed terminal differentiation of cardiomyocytes.

TABLE 1

Filtered Exosome Sequencing Results

| Gene | Accession number | Variant cDNA | Variant protein | Allele frequency in 1000 Genomes November 2010 | Present in Affected Sibling |
|---|---|---|---|---|---|
| ALMS1 | NM_015120 | c.1794_1801dup8 | p.Lys601Arg_fsX3 | — | Yes |
|  | NM_015120 | c.11116_11134del19 | p.Arg3706Leu_fsX11 | — | Yes |
| CD248 | NM_020404 | c.683C > G | p.Pro228Leu | — | No |
|  | NM_020404 | c.1235C > G | p.Pro412Arg | — | No |
| FERMT1 | NM_017671 | c.292C > T | p.Arg98Cys | — | Yes |
|  | NM_017671 | c.1555G > T | p.Val519Leu | — | Yes |
| FRMD4B | NM_015123 | c.1424C > T | p.Pro475Leu | 0.6 | Not tested |
|  | NM_015123 | c.2309A > C | p.Asn770Thr | — | Yes |
| RGS3 | NM_144489 | c.231G > T | p.Gln77His | 1.2 | Not tested |
|  | NM_021106 | c.1327G > T | p.Ala443Ser | 0.1 | Not tested |

TABLE 1-continued

Filtered Exosome Sequencing Results

| Gene | Accession number | Variant cDNA | Variant protein | Allele frequency in 1000 Genomes November 2010 | Present in Affected Sibling |
|---|---|---|---|---|---|
| RYR3 | NM_001036 | c.4529T > C | p.Val1510Ala | — | Yes |
|  | NM_001036 | c.14128G > A | p.Asp4710Asn | — | No |
| SNX19 | NM_014758 | c.842C > T | p.Ala281Val | 0.5 | Not tested |
|  | NM_014758 | c.2683C > T | p.Arg895Trp | — | No |

Genes in which two rare variants are present in the proband, inherited in a recessive manner from each parent. Variants present in the 1000 Genomes dataset by 11/2010 were prioritized lower. Those in which one or both variants was not present in the affected sibling were excluded.

Figure 6:
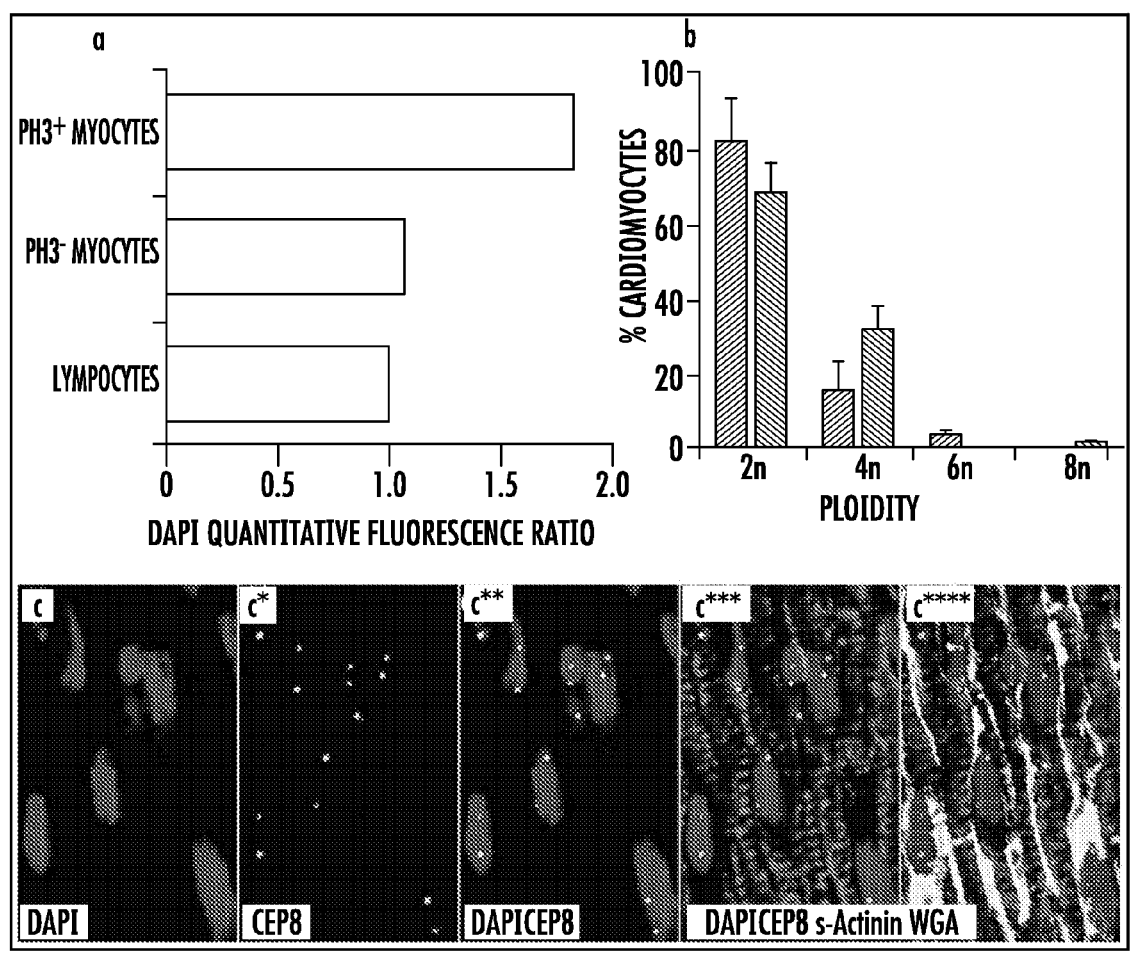
FIG. 6. Human cells analyzed for ploidy status. (A) The DNA content in dividing cardiomyocyte nuclei was compared to non-dividing nuclei (both cardiomyocytes and non-cardiomyocytes) in the proband using quantitative confocal laser cytometry with DAPI nuclear staining The ratio of DNA in nuclei from proliferating cardiomyocytes compared to non-proliferating (cardiomyocyte and lymphocyte) nuclei in the proband is 1.9, indicating predominantly 4N chromosomal content in these cells. (B) Summary of the ploidy analysis using centromeric probes for 4 affected individuals and 2 unaffected controls. (C) An example of ploidy analysis using one of the centromere FISH probes for chromosome 8 (CEP8) in an affected individual.

Mitogenic Cardiomyopathy is Associated with ALMS1 Mutations. To extend these findings, we sequenced ALMS1 in four additional infants (two sibling pairs) with mitogenic cardiomyopathy, from whom DNA was available (5). We identified homozygous or compound heterozygous mutations in each of them (Table 2). Using the same method described above, we quantified PH3-positive cardiomyocytes in three affected individuals (one from each sib-pair) to the three age-matched controls with heart failure, and found it to be higher in the affected children (71.3+8.6 per mm$^2$ compared to 0.28+0.07 per mm$^2$, respectively) (FIG. 1g). Accordingly, DNA content in dividing cardiomyocytes was 1.9-fold greater in PH3-positive myocytes than in non-dividing cells, confirming that PH3-positive myocytes are undergoing mitosis (FIG. 6).

TABLE 2

Mutations in ALMS1 in People with Mitogenic Cardiomyopathy

| Individual | Exon | cDNA | protein |
|---|---|---|---|
| 1a | 8 | 1794_1801dup8 | Lys601Arg_fsX3 |
|  | 16 | 11116_11134del19 | Arg3706Leu_fsX11 |
| 1b | 8 | 1794_1801dup8 | Lys601Arg_fsX3 |
|  | 16 | 11116_11134del19 | Arg3706Leu_fsX11 |
| 2a | 8 | 4296_4299delCACA | His1432Gln_fsX40 |
|  | 8 | 5926delG | Glu1976Ser_fsX8 |
| 2b | 8 | 4296_4299delCACA | His1432Gln_fsX40 |
|  | 8 | 5926delG | Glu1976Ser_fsX8 |
| 3a | 8 | 1894C > T | Gln632Ter |
|  | 8 | 1894C > T | Gln632Ter |
| 3b | 8 | 1894C > T | Gln632Ter |
|  | 8 | 1894C > T | Gln632Ter |

Cardiomyocytes can undergo DNA replication without completing the cell cycle. Polyploidization occurs during early postnatal development and in response to myocardial stress (4, 18, 19). We considered the possibility that ALMS1-deficiency could result in increased polyploidy. We applied centromeric FISH probes to determine the ploidy status in these infants with mitogenic cardiomyopathy. The percentage of 4N cardiomyocytes was 31.1+7.2% among the four affected individuals and 15.5+8.3% in the controls, P=0.26. Although we found cardiomyocytes that were polyploid (>4N), there was no difference between affected individuals (0.4%, n=4) and failing heart age matched controls (0.6%, n=2) (FIG. 6). Taken together, these results indicate that ALMS1 deficiency in cardiomyocytes does not lead to increased polyploidy.

Figure 7:
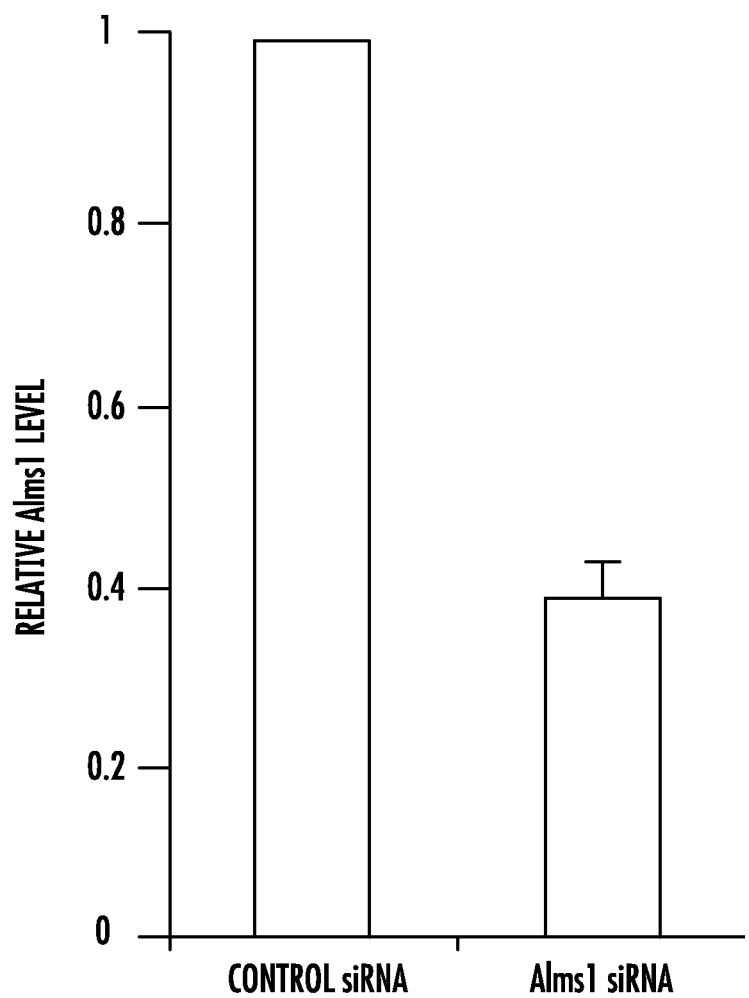
FIG. 7. Knockdown of Alms1 in cardiomyocytes. Relative mRNA levels of Alms1 24 h after siRNA treatment of neonatal cardiomyocyte enriched cultures (N=3), normalized to Gapdh mRNA level.
Figure 8:
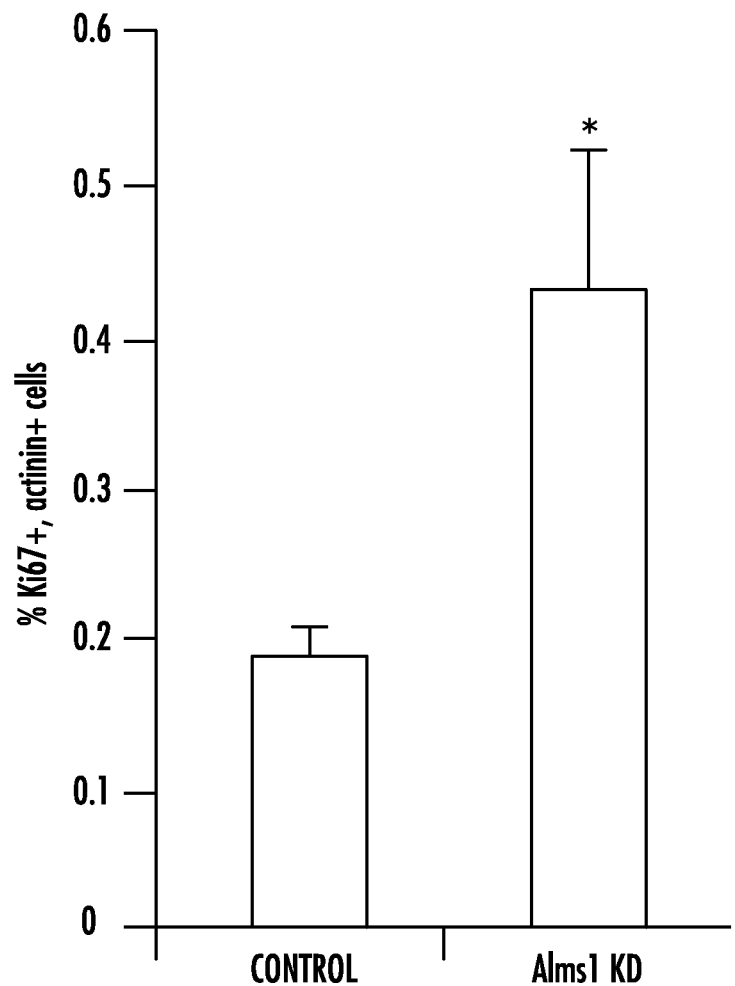
FIG. 8. Alms1 siRNA increases markers of proliferation in cultured cardiomyocytes. Cultured murine cardiomyocytes were evaluated after 48 hours for proliferation by immunostaining for Ki67 together with α-sarcomeric actinin to identify cardiomyocytes proceeding through the cell cycle. Flow cytometry analyses identified a 2.5-fold increase in the number of cardiomyocytes expressing the proliferation marker Ki67 after Alms1 siRNA knockdown compared to control (4.2% vs. 1.7% respectively; P=0.048).
Figure 9:
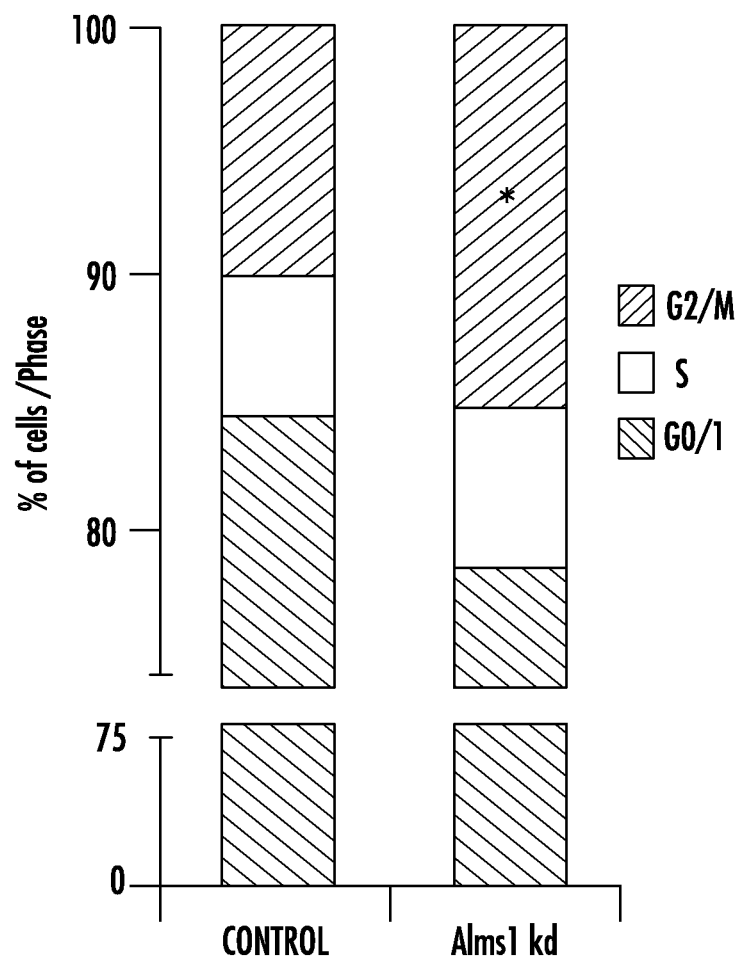
FIG. 9. Knockdown of Alms1 increases the number of cells in G2/M phases in cardiomyocyte enriched cultures. Comparison of the % of cells in different phases of cell cycle between control transfection and Alms1 knockdown (KD) using siRNA. (*) refers to P<0.05.

ALMS1 Loss Extends Postnatal Cardiomyocyte Proliferation. To confirm that ALMS1 loss is sufficient for extending the postnatal proliferative window of cardiomyocytes, we treated cultured neonatal mouse cardiomyocytes with Alms1 siRNA (FIG. 7). After 48 hours, cells were stained with antibodies against Ki67 (a wide-ranging marker of proliferation) or Vybrant DyeCycle Ruby Stain (a marker of DNA content for determination of cell cycle; Invitrogen), together with cTnT, and analyzed by flow cytometry. In ALMS1-deficient cardiomyocytes, Ki67-positive cardiomyocytes were 2.5-fold higher compared to control (4.2% vs. 1.7% respectively; P<0.05) (FIG. 8). Likewise, we observed more cells in G2/M phases after Alms1 knockdown compared to the control (13.3+1.8% vs. 9.6+1.3% respectively; P<0.05) (FIG. 9). We also analyzed Ki67 expression in cells stained with the fibroblast marker Thy-1 (20) and found no significant difference between ALMS1-deficient cardiac fibroblasts compared to control (3.5+0.5% vs. 2.9+0.8% respectively; P=0.55), indicating that the observed increase of cells in G2/M may be in cardiomyocytes. To determine whether the observed increase in G2/M was mediated by cardiomyocytes, we cultured neonatal mouse cardiomyocytes obtained from transgenic mice in which the aMHC promoter drives expression of green fluorescent protein (GFP), and thus only cardiomyocytes produce GFP (21). After Alms1 knockdown, the number of GFP-positive cells in phases G2/M was increased compared to the control (11.3+1.0% vs. 7.0+0.9% respectively, P<0.05) (FIG. 2a), indicating that ALMS1-deficiency leads to impaired cell cycle arrest in cardiomyocytes.

Figure 2:
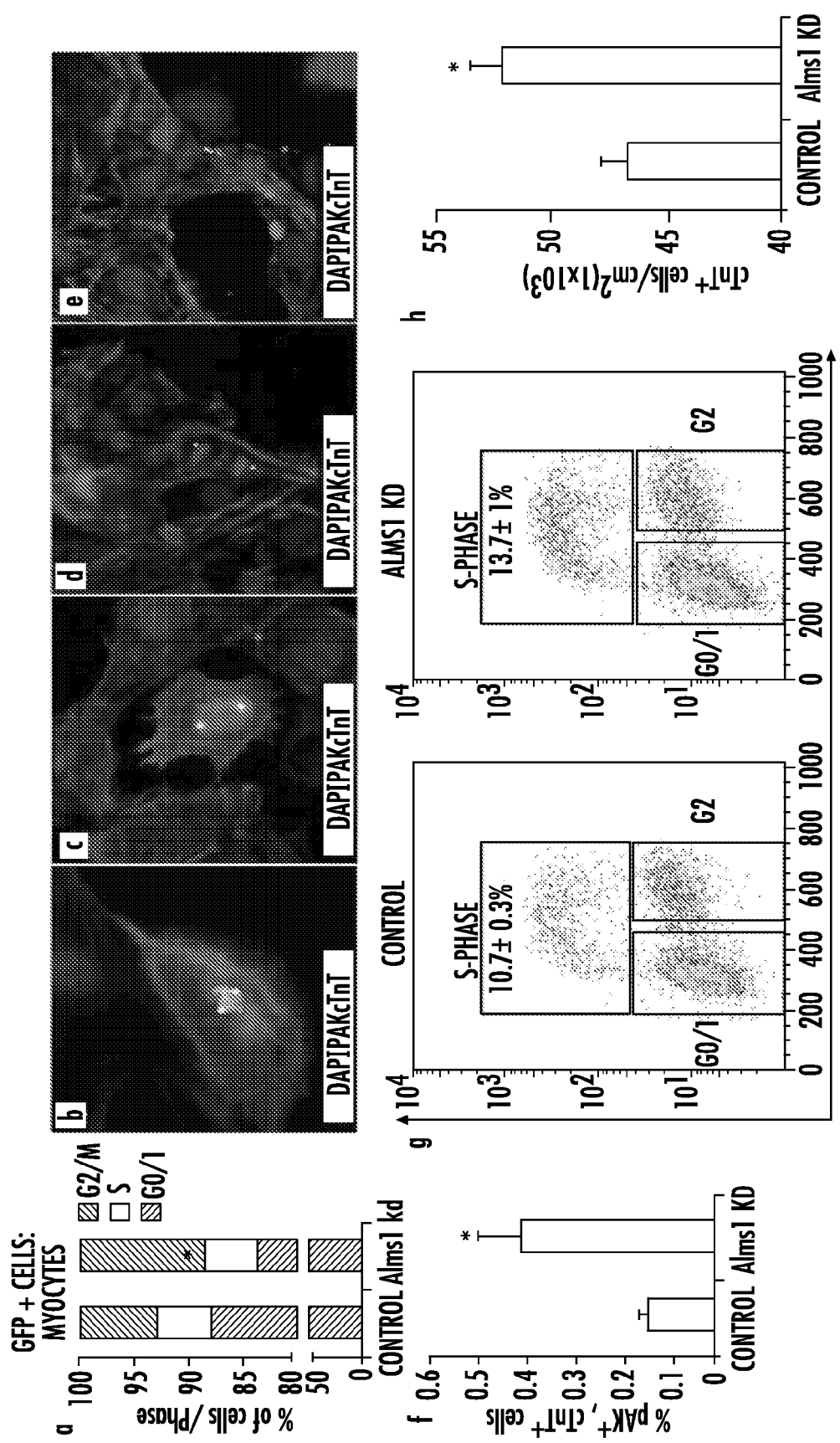
FIG. 2. Increased cardiomyocyte proliferation in cultured cells after Alms1 knockdown. (A) Comparison of α-MHC-GFP positive cardiomyocytes in different phases of cell cycle after control siRNA transfection compared with Alms1 knockdown (KD) by siRNA. Alms1 KD increases the proportion of cells in G2/M phase. (B, C, D, E) PAK-positive cardiomyocytes in different phases of mitosis; b is prophase, c is metaphase, d is anaphase, e is telophase. (F) Flow cytometry of puromycin-selected cardiomyocytes (cTnT+ cells) shows that after Alms1 knockdown (KD), there is increased PAK expression compared to controls. (G) Scatter plot showing increased incorporation of EdU and increased DNA content in puromycin-selected (cTnT+) cardiomyocytes with ALMS1 knockdown (KD). (H) Total number of puromycin-selected cardiomyocytes after Alms1 knockdown (KD) is increased compared to controls. In all Figures, (*) refers to P<0.05. Error bars represent standard error of mean (SEM).
Figure 10:
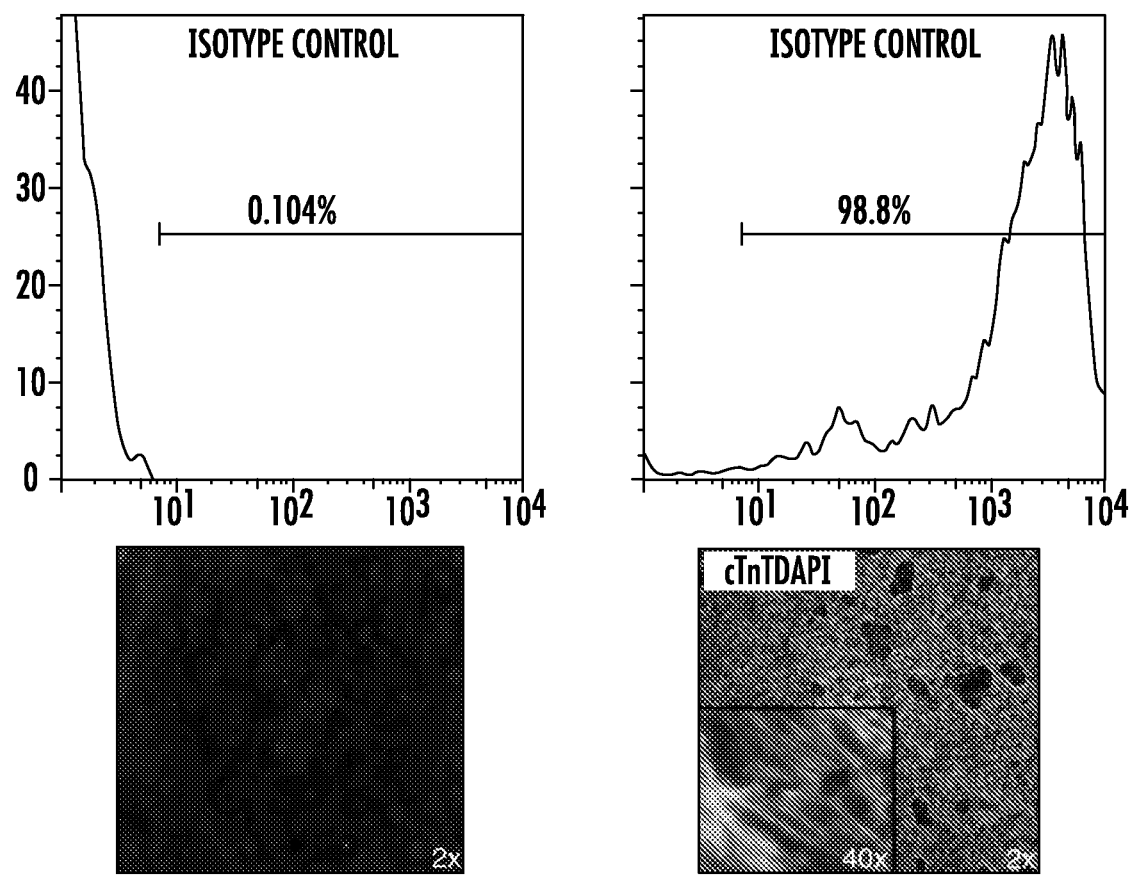
FIG. 10. Cardiomyocytes derived from ES cells with puromycin selection. The purification of cardiomyocytes was confirmed by flow cytometry (98.8% cTnT+cells) and immunohistochemistry. Puromycin-selected cells were stained with antibodies against cTnT or isotype control antibodies followed by staining with Alexa-Fluor 488 (Invitrogen). The percentage of cTnT+cells (cardiomyocytes) 48 h after puromycin selection is 98.8%.

To confirm that ALMS1-deficient cardiomyocytes proliferate with impaired cell cycle arrest, we differentiated cardiomyocytes from mouse ESCs that carry a cardiomyocyte-specific promoter (Ncx1), which drives puromycin resistance, allowing efficient purification of cardiomyocytes (>98%) (22). (FIG. 10) By immunohistochemistry, we confirmed the presence of cardiomyocytes in pro-, meta-, ana- and telophase of mitosis after knockdown of Alms1 (FIG. 2b,c,d,e), demonstrating that these cardiomyocytes complete the cell cycle in vitro. In accordance with this observation, the amount PAK-positive cardiomyocytes was higher in ALMS1-deficient cardiomyocytes compared to control (0.41+0.15% vs. 0.15+0.04%; P<0.05; FIG. 2f).

To confirm that ALMS1 loss extends the proliferative window of cardiomyocytes, we treated puromycin-selected cardiomyocytes with Alms1 siRNA or control siRNA. After 48 hours, we pulse-labeled cardiomyocytes with 5-ethynyl-2'-deoxyuridine (EdU) for 12 h. We observed an increase in EdU-positive cardiomyocytes after Alms1 knockdown compared to controls (13.7±1.0% vs. 10.7±0.3%, P<0.05)(FIG. 2g). During maturation, cardiomyocytes undergo karyokinesis (nuclear division) but not cytokinesis (cell division) and become terminally differentiated (23). To exclude the possibility that the observed increase in EdU-positive uptake is due to karyokinesis and not cytokinesis, we counted cardiomyocytes 72 hours after siRNA treatment and found that the number of cardiomyocytes was higher after Alms1 knockdown compared to control (51,915+1821/cm$^2$ vs. 46,696+1311/cm$^2$, respectively; P<0.05) (FIG. 2h). Taken together, these results confirm that ALMS1-deficiency increases cardiomyocyte proliferation in vitro.

Figure 3:
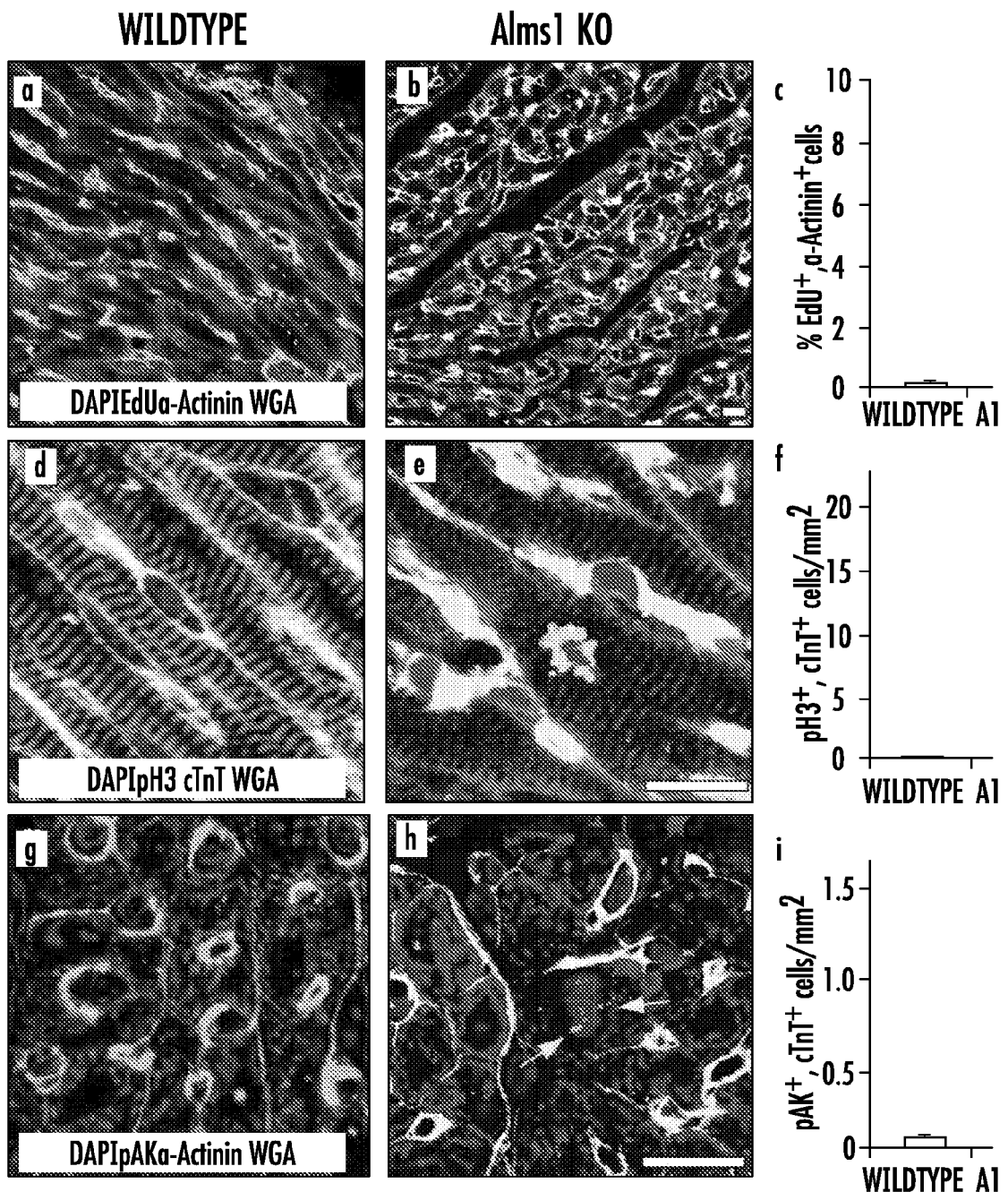
FIG. 3. Increased cardiomyocyte proliferation in homozygous Alms1$^{Gt/Gt}$ mutant mice. (A, B) Representative confocal images demonstrating EdU incorporation in Alms1$^{Gt/Gt}$ vs. wild-type littermate control mouse cardiac myocytes. (C) Bar graph comparing cardiomyocyte EdU incorporation in Alms1$^{Gt/Gt}$ mutant (KO) vs. wild-type littermate control mice. (D, E) Representative confocal images demonstrating PH3 in a cardiomyocyte nucleus in a Alms1$^{Gt/Gt}$ mutant vs. wild-type littermate control mouse. (F) Comparison of the number of PH3-positive cardiomyocytes in Alms1$^{Gt/Gt}$ (KO) vs. wild-type littermate control mice. (G, H) Representative confocal images demonstrating PAK staining is present in a dividing cardiomyocyte nucleus in an Alms1$^{Gt/Gt}$ mouse (KO); DAPI highlights the nucleus, which is surrounded by α-sarcomeric actinin to highlight cardiomyocytes and WGA to identify cell boundaries. (I.) Comparison of the number of PAK-positive cardiomyocytes in Alms1$^{Gt/Gt}$ (KO) vs. wild-type controls. All scale bars represent 10 µm. Error bars represent standard error of mean (SEM).
Figure 11A:
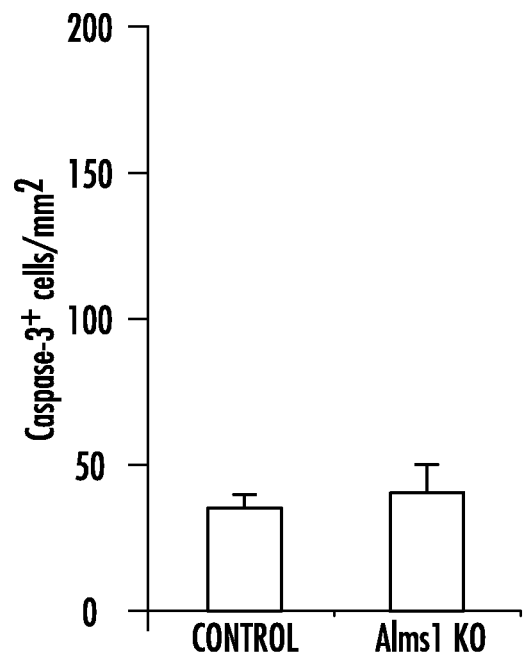
FIG. 11A. Analysis of caspace-3 as a marker of apoptosis. Postnatal day 15 mouse hearts were analyzed for caspace-3, a marker of apoptosis, by immunostaining The number of positively stained cells was normalized per mm². Positive staining was low for both the Alms1$^{Gt/Gt}$ (KO) and wild-type littermate control mice.
Figure 11B:
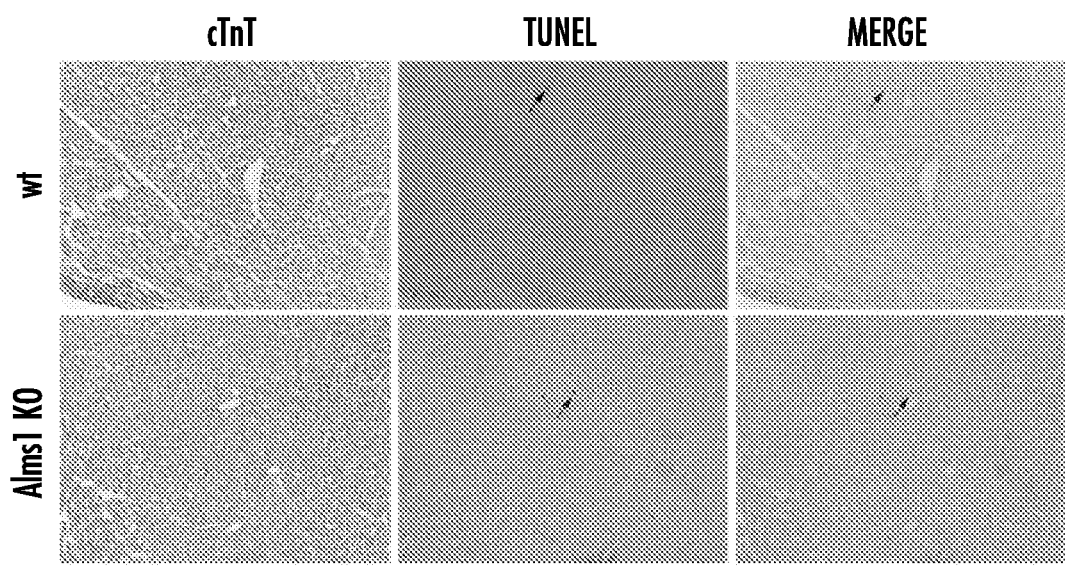
FIG. 11B. Analysis of TUNEL positivity as a marker of apoptosis. Postnatal day 15 mouse hearts were analyzed for TUNEL, another marker of apoptosis, by immunostaining, with cardiomyocytes designated by cTnT. Positive staining was low for both the Alms1$^{Gt/Gt}$ (KO) and wild-type littermate control mice.

Impaired Cardiomyocyte Cell Cycle Arrest in Alms1$^{Gt/Gt}$ Mice. To investigate the role of ALMS1 in vivo, we utilized Alms1$^{Gt/Gt}$ mice with truncated Alms1 mRNA and many characteristics of human Alström syndrome (24). In mice, the maturation process from mono- to binucleate state occurs during postnatal day 5-10, resulting in 95-99% cardiomyocytes being binucleated and terminally differentiated at 10 days of age (19, 25). We therefore analyzed mouse hearts at 15.5 days of age for persistent cardiomyocyte proliferation. To do this, we treated 15-day old mice with a pulse-dose of EdU, and 12 hours later, their hearts were isolated and EdU uptake in cardiomyocytes was analyzed using the double-blinded quantification method described above. In the Alms1$^{Gt/Gt}$ mutant mice, more than 8% of cardiomyocytes were EdU-positive, compared to very low levels in the wild-type littermate controls (8.3+0.91% vs. 0.3+0.04%, respectively; FIG. 3a, b, and c). Accordingly, we also observed a higher number of PH3-positive cardiomyocytes in homozygous Alms1$^{Gt/Gt}$ mutant mice compared to their wild-type littermates (13.2 compared to less than 1 per mm$^2$; P<0.01) (FIG. 3d, e, and f). Additional staining demonstrated increased PAK-positive cardiomyocytes in the Alms1$^{Gt/Gt}$ mice compared to wild-type controls (1.36+0.1 vs. 0.11+0.1 per mm2, respectively; P<0.001)(FIG. 3g, h, and i). Importantly, we did not observe any difference in apoptosis (caspase3-positive cells) between Alms1$^{Gt/Gt}$ mutant mice and their littermate controls (FIG. 11).

Figure 4:
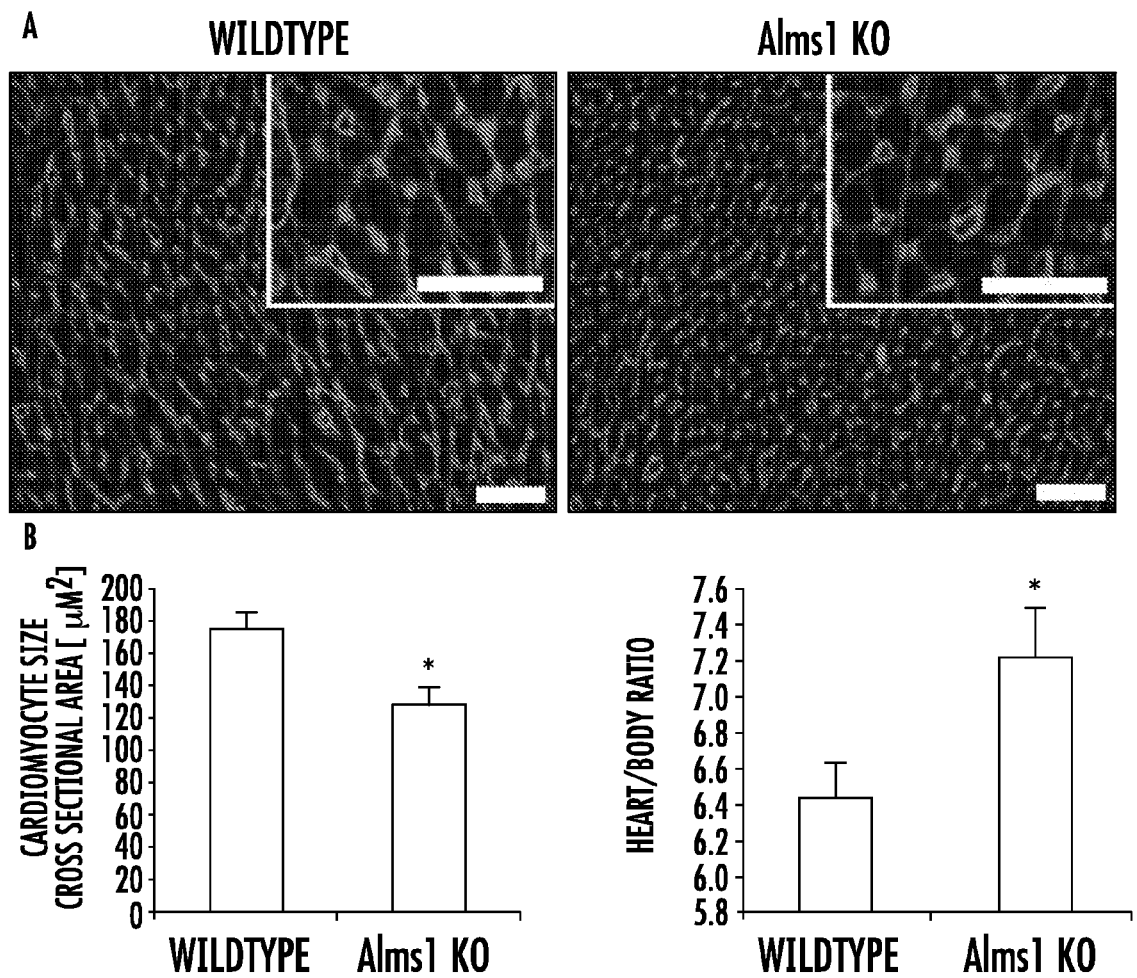
FIG. 4. Increased cardiomyocyte density and normalized heart size in homozygous Alms1Gt/Gt mutant mice. (A) Representative images of wild-type and Alms1Gt/Gt hearts stained with wheat germ agglutinin. (B) Measured cardiomyocyte cross sectional area. (C) Heart/body weight ratios. Scale bar=50 µM.

Phenotypic characterization of Alms1Gt/Gt at postnatal day 15.5 demonstrated that ALMS1-mutant mouse heart/body ratio was larger in Alms1Gt/Gt mice (7.2±0.3 vs. 6.4±0.2; P=0.037) (FIG. 4). In addition, Alms1Gt/Gt cardiomyocytes were smaller compared to wild-type littermate controls (128.2±10.6 vs. 176.1±8.5 µM2, P<0.0.001) (FIG. 4), implying that cardiomyocyte number is increased in Alms1Gt/Gt hearts. Together, these findings indicate that terminal differentiation is impaired in ALMS1-deficient cardiomyocytes and that ALMS1-deficient cardiomyocytes remain proliferative beyond the normal window of postnatal cardiomyocyte cell cycle arrest.

We considered whether our findings could be due to an increased number of cardiac stem cells. However we observed no difference in the number of c-kit+ or Sca-1+ cardiac stem cell markers in Alms1$^{Gt/Gt}$ compared to littermates (both markers <1 cell per 225 µM$^2$). As cardiac stem cells differentiate, they may lose c-kit or Sca-1 markers. Thus, we cannot exclude that the increase in proliferating cardiomyocytes may arise in part from resident cardiac stem cells.

Discussion

Figure 12:
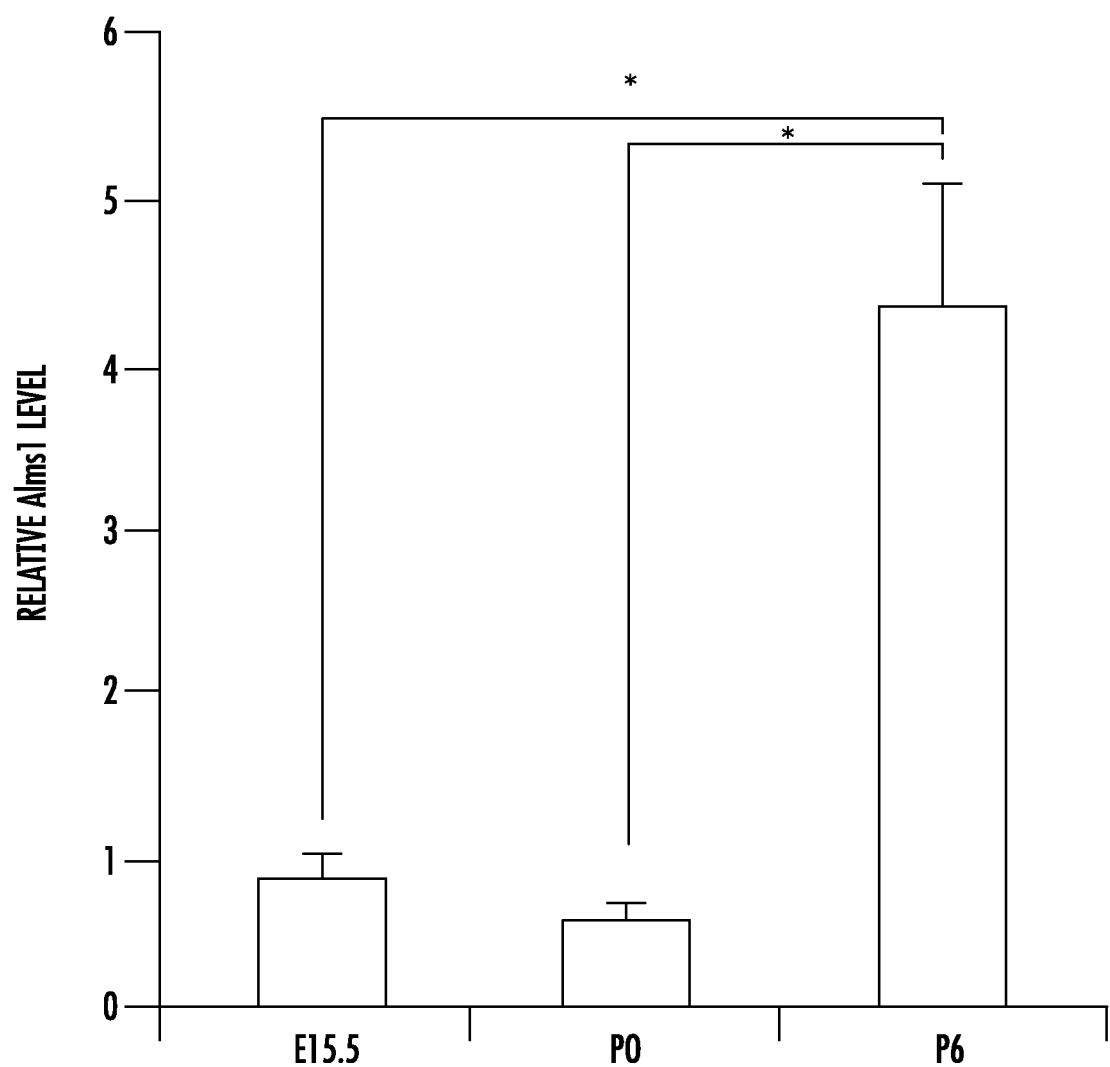
FIG. 12. Perinatal expression of Alms1 in murine cardiomyocytes. Murine GFP-positive cardiomyocytes were isolated from α-MHC-GFP transgenic mice by FACS. Alms1 mRNA levels were normalized to Gapdh. Relative Alms1 mRNA levels at embryonic day 15.5 (ED 15.5; N=4) and postnatal day 0 (P0; N=4) were compared by student's T-Test to postnatal days 5.5/6.5 (P5/6; N=10), p=0.02 and p=0.013, respectively. (*) denotes P<0.05. There was no significant difference in Alms1 expression between days E15.5 and P0.

Our data show that ALMS1 is a key molecule for cell cycle regulation in perinatal cardiomyocytes. Alms1 levels in dividing cardiomyocytes obtained from proliferative mouse hearts (embryonic day 15.5) are relatively low, compared to levels at the beginning of the maturation process (postnatal day 6) when cytokinesis rapidly declines, suggesting that ALMS1 may be transcriptionally regulated during perinatal development (FIG. 12). ALMS1 is a component of the non-motile primary cilium, a subcellular organelle that projects from most cell types. Its presence is temporally associated with cellular quiescence, with resorption during mitosis 26. Induction of a longer cilium causes delay in G1/S transition, and ciliary disassembly increases S-phase (27, 28). Prior reports show that certain components of the primary cilium restrain canonical Wnt/β-catenin signaling, which plays an important role in cardiomyogenesis (29, 30). Deficiency of ALMS1 may activate Wnt/β-catenin signaling, thereby activating the transcription factor TCF/LEF (T-cell factor/lymphoid enhancer factor) and inducing transcription of genes that promote cell cycle proliferation (31, 32).

ALMS1 also localizes to the centrosome, which plays a pivotal role in regulation of the cell cycle (33, 34). At postnatal day 15 (1 week beyond the normal window of postnatal cardiomyocyte cell cycle arrest), ALMS1-deficient mice display persistent cardiomyocyte proliferation, indicating that ALMS1-deficient cardiomyocytes may have an impaired ability to undergo cell cycle arrest. A similar finding was previously reported for the transcription factor MEIS 1, although no direct link between MEIS 1 and ALMS1 is currently known (6). Throughout mitosis, ALMS1 localizes to the centrosomal spindle poles, and during late mitosis, ALMS1 localizes to the contractile ring and the cleavage furrow (35). ALMS1 retains the centrosome cohesion protein C-NAP1, an important regulator of centrosome organization during mitosis. Depletion of ALMS1 reduces centrosomal levels of C-NAP1 and increases centrosome splitting, a key event for chromosomal division during anaphase (33). In addition, ALMS1 interacts with several cytoskeleton-associated components that are necessary for the recycling of receptors to the plasma membrane, also referred to as endocytic trafficking (35). During mitosis endocytic trafficking is repressed, as continued endocytosis may interfere with accurate chromosome segregation (36-38). Interestingly, endocytic trafficking is significantly reduced in ALMS1-deficient cells (35). Whether the impairment of terminal differentiation of cardiomyocyte proliferation is partly due to diminished endocytic trafficking remains unclear. Further investigation of this role of ALMS1 may identify novel and therapeutically important avenues to alter cardiomyocyte cell cycle activity.

REFERENCES

1. Drenckhahn, J. D. et al. Compensatory growth of healthy cardiac cells in the presence of diseased cells restores tissue homeostasis during heart development. Dev Cell 15, 521-33 (2008).

2. Meilhac, S. M. et al. A retrospective clonal analysis of the myocardium reveals two phases of clonal growth in the developing mouse heart. Development 130, 3877-89 (2003).

3. Pasumarthi, K. B. & Field, L. J. Cardiomyocyte cell cycle regulation. Circ Res 90, 1044-54 (2002).

4. Soonpaa, M. H. & Field, L. J. Survey of studies examining mammalian cardiomyocyte DNA synthesis. Circ Res 83, 15-26 (1998).

5. Chang, K. T., Taylor, G. P., Meschino, W. S., Kantor, P. F. & Cutz, E. Mitogenic cardiomyopathy: a lethal neonatal familial dilated cardiomyopathy characterized by myocyte hyperplasia and proliferation. Hum Pathol 41, 1002-8 (2010).

6. Mahmoud, A. I. et al. Meis1 regulates postnatal cardiomyocyte cell cycle arrest. Nature 497, 249-53 (2013).

7. Wei, Y., Mizzen, C. A., Cook, R. G., Gorovsky, M. A. & Allis, C. D. Phosphorylation of histone H3 at serine 10 is correlated with chromosome condensation during mitosis and meiosis in Tetrahymena. Proc Natl Acad Sci USA 95, 7480-4 (1998).

8. Kim, Y., Holland, A. J., Lan, W. & Cleveland, D. W. Aurora kinases and protein phosphatase 1 mediate chromosome congression through regulation of CENP-E. Cell 142, 444-55 (2010).

9. Yang, K.-T. et al. Aurora-C Kinase Deficiency Causes Cytokinesis Failure in Meiosis I and Production of Large Polyploid Oocytes in Mice. Mol Biol Cell 21, 2371-2383 (2010).

10. Seki, A., Coppinger, J. A., Jang, C. Y., Yates, J. R. & Fang, G. Bora and the kinase Aurora a cooperatively activate the kinase Plk1 and control mitotic entry. Science 320, 1655-8 (2008).

11. Zimmerman, R. S. et al. A novel custom resequencing array for dilated cardiomyopathy. Genetics in Medicine 12, 268-278 (2010).

12. Collin, G. B. et al. Mutations in ALMS1 cause obesity, type 2 diabetes and neurosensory degeneration in Alstrom syndrome. Nat Genet 31, 74-8 (2002).

13. Marshall, J. D. et al. Spectrum of ALMS1 variants and evaluation of genotype-phenotype correlations in Alstrom syndrome. Hum Mutat 28, 1114-23 (2007).

14. Alstrom, C. H., Hallgren, B., Nilsson, L. B. & Asander, H. Retinal degeneration combined with obesity, diabetes mellitus and neurogenous deafness: a specific syndrome (not hitherto described) distinct from the Laurence-Moon-Bardet-Biedl syndrome: a clinical, endocrinological and genetic examination based on a large pedigree. Acta Psychiat. Neurol. Scand. 34, 1-35 (1959).

15. Girard, D. & Petrovsky, N. Alstrom syndrome: insights into the pathogenesis of metabolic disorders. Nat Rev Endocrinol 7, 77-88 (2011).

16. Marshall, J. D., Maffei, P., Collin, G. B. & Naggert, J. K. Alstrom syndrome: genetics and clinical overview. Curr Genomics 12, 225-35 (2011).

17. Bond, J. et al. The importance of seeking ALMS1 mutations in infants with dilated cardiomyopathy. J Med Genet 42, 10 (2005).

18. Li, F., Wang, X., Capasso, J. M. & Gerdes, A. M. Rapid transition of cardiac myocytes from hyperplasia to hypertrophy during postnatal development. J Mol Cell Cardiol 28, 1737-46 (1996).

19. Soonpaa, M. H., Kim, K. K., Pajak, L., Franklin, M. & Field, L. J. Cardiomyocyte DNA synthesis and binucleation during murine development. Am J Physiol 271, H2183-H2189 (1996).

20. Ieda, M. et al. Cardiac Fibroblasts Regulate Myocardial Proliferation through $^2$1 Integrin Signaling. Developmental Cell 16, 233-244 (2009).

21. Ieda, M. et al. Direct reprogramming of fibroblasts into functional cardiomyocytes by defined factors. Cell 142, 375-86 (2010).

22. Boheler, K. R. et al. Embryonic stem cell-derived cardiomyocyte heterogeneity and the isolation of immature and committed cells for cardiac remodeling and regeneration. Stem Cells Int 2011, 214203 (2011).

23. Walsh, S., Pontén, A., Fleischmann, B. K. & Jovinge, S. Cardiomyocyte cell cycle control and growth estimation in vivo—an analysis based on cardiomyocyte nuclei. Cardiovasc Res 86, 365-73 (2010).

24. Collin, G. B. et al. Alms1-disrupted mice recapitulate human Alstrom syndrome. Hum Mol Genet 14, 2323-33 (2005).

25. Walsh, S., Pontén, A., Fleischmann, B. K. & Jovinge, S. Cardiomyocyte cell cycle control and growth estimation in vivo—an analysis based on cardiomyocyte nuclei. Cardiovasc Res 86, 365-373 (2010).

26. Rash, J. E., Shay, J. W. & Biesele, J. J. Cilia in cardiac differentiation. J Ultrastruct Res 29, 470-84 (1969).

27. Kim, S. et al. Nde1-mediated inhibition of ciliogenesis affects cell cycle re-entry. Nat Cell Biol 13, 351-360 (2011).

28. Li, A. et al. Ciliary transition zone activation of phosphorylated Tctex-1 controls ciliary resorption, S-phase entry and fate of neural progenitors. Nat Cell Biol 13, 402-411 (2011).

29. Ajima, R. & Hamada, H. Wnt signalling escapes to cilia. Nat Cell Biol 13, 636-637 (2011).

30. Kwon, C. et al. Canonical Wnt signaling is a positive regulator of mammalian cardiac progenitors. Proc Natl Acad Sci USA 104, 10894-9 (2007).

31. Logan, C. Y. & Nusse, R. The Wnt signaling pathway in development and disease. Annu Rev Cell Dev Biol 20, 781-810 (2004).

32. Hayward, P., Kalmar, T. & Arias, A. M. Wnt/Notch signalling and information processing during development. Development 135, 411-24 (2008).

33. Knorz, V. J. et al. Centriolar association of ALMS1 and likely centrosomal functions of the ALMS motif-containing proteins C10orf90 and KIAA1731. Mol Biol Cell 21, 3617-29 (2010).

34. Hinchcliffe, E. H. Cell cycle: seeking permission from the mother centriole. Current Biology 13, R646-648 (2003).

35. Collin, G. B. et al. The Alström Syndrome Protein, ALMS1, Interacts with α-Actinin and Components of the Endosome Recycling Pathway. PLoS One 7, e37925 (2012).

36. Fielding, A. B., Willox, A. K., Okeke, E. & Royle, S. J. Clathrin-mediated endocytosis is inhibited during mitosis. Proc Natl Acad Sci USA 109, 6572-7 (2012).

37. Fielding, A. B. & Royle, S. J. Mitotic inhibition of clathrin-mediated endocytosis. Cell Mol Life Sci 70, 3423-33 (2013).

38. Sager, P. R., Brown, P. A. & Berlin, R. D. Analysis of transferrin recycling in mitotic and interphase HeLa cells by quantitative fluorescence microscopy. Cell 39, 275-82 (1984).

39. Li, H. & Durbin, R. Fast and accurate long-read alignment with Burrows-Wheeler transform. Bioinformatics 26, 589-595 (2010).

40. Li, H. et al. The Sequence Alignment/Map format and SAMtools. Bioinformatics 25, 2078-2079 (2009).

41. Simpson, P. & Savion, S. Differentiation of rat myocytes in single cell cultures with and without proliferating nonmyocardial cells. Cross-striations, ultrastructure, and chronotropic response to isoproterenol. Circulation Research 50, 101-116 (1982).

42. Yamanaka, S., Zahanich, I., Wersto, R. P. & Boheler, K. R. Enhanced Proliferation of Monolayer Cultures of Embryonic Stem (ES) Cell-Derived Cardiomyocytes Following Acute Loss of Retinoblastoma. PLoS One 3, e3896 (2008).

43. Kwon, C. et al. Notch post-translationally regulates beta-catenin protein in stem and progenitor cells. Nat Cell Biol 13, 1244-51 (2011).

44. Kattman, S. J. et al. Stage-specific optimization of activin/nodal and BMP signaling promotes cardiac differentiation of mouse and human pluripotent stem cell lines. Cell Stem Cell 8, 228-40 (2011).

45. Jagger, D. et al. Alstrom Syndrome protein ALMS1 localizes to basal bodies of cochlear hair cells and regulates cilium-dependent planar cell polarity. Hum Mol Genet 20, 466-81 (2011).

46. Shenje, L. T. et al. Lineage tracing of cardiac explant derived cells. PLoS One 3, e1929 (2008).

We claim:

1. A method for inducing proliferation of cardiomyocytes comprising the step of administering an effective amount of an Alstrom syndrome 1 protein (ALMS1) inhibitor, wherein the ALMS1 inhibitor is an antisense oligonucleotide.

2. A method for inducing proliferation of cardiomvocytes in a patient suffering from heart failure, cardiomyopathy, congenital heart disease or cardiac injury comprising the step of administering to the patient a therapeutically effective amount of an ALMS1 inhibitor, wherein the ALMS1 inhibitor is an siRNA, shRNA or an antisense oligonucleotide.

3. A method for treating heart failure, cardiomyopathy, congenital heart disease or cardiac injury in a patient comprising the step of administering to the patient a therapeutically effective amount of an ALMS1 inhibitor, wherein the ALMS1 inhibitor is an siRNA, and further wherein the ALMS1 inhibitor inhibits ALMS1 expression and/or activity and induces proliferation of cardiomyocytes.

4. A method for treating heart failure, cardiomyopathy, congenital heart disease or cardiac injury in a patient comprising the step of administering to the patient a therapeutically effective amount of an ALMS1 inhibitor, wherein the ALMS1 inhibitor is shRNA, and further wherein the ALMS1 inhibitor inhibits ALMS1 expression and/or activity and induces proliferation of cardiomyocytes.

5. A method for treating heart failure, cardiomyopathy, congenital heart disease or cardiac injury in a patient comprising the step of administering to the patient a therapeutically effective amount of an ALMS1 inhibitor, wherein the ALMS1 inhibitor is an antisense oligonucleotide, and further wherein the ALMS1 inhibitor inhibits ALMS1 expression and/or activity and induces proliferation of cardiomyocytes.

6. A method for inducing proliferation of cardiomyocytes comprising the step of administering an effective amount of an siRNA or shRNA inhibitor of the expression of the ALMS1 gene to result in RNA interference.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Potential RNAi target
<220> FEATURE:
<221> NAME/KEY: misc_feature
<222> LOCATION: (3)..(21)
<223> OTHER INFORMATION: "n" is any nucleotide

<400> SEQUENCE: 1
aannnnnnnn nnnnnnnnnn ntt                                    23

<210> SEQ ID NO 2
<211> LENGTH: 23
<212> TYPE: DNA
<213> ORGANISM: Artificial sequence
<220> FEATURE:
<223> OTHER INFORMATION: Potential RNAi target
<220> FEATURE:
<221> NAME/KEY: misc_feature
<222> LOCATION: (3)..(23)
<223> OTHER INFORMATION: "n" is any nucleotide

<400> SEQUENCE: 2
aannnnnnnn nnnnnnnnnn nnn                                    23
```